United States Patent [19]

Suzuki et al.

[11] Patent Number: 5,431,806
[45] Date of Patent: Jul. 11, 1995

[54] OXYGEN ELECTRODE AND TEMPERATURE SENSOR

[75] Inventors: Hiroaki Suzuki; Akio Sugama; Naomi Kojima, all of Kawasaki, Japan

[73] Assignee: Fujitsu Limited, Kawasaki, Japan

[21] Appl. No.: 153,144

[22] Filed: Nov. 17, 1993

Related U.S. Application Data

[63] Continuation-in-part of Ser. No. 993,486, Dec. 17, 1992, Pat. No. 5,358,619, which is a continuation-in-part of Ser. No. 761,005, Sep. 17, 1991, abandoned.

[30] Foreign Application Priority Data

| Sep. 17, 1990 | [JP] | Japan | 2-243849 |
| Jun. 24, 1991 | [JP] | Japan | 3-151573 |
| Dec. 20, 1991 | [JP] | Japan | 3-338678 |
| Jul. 22, 1992 | [JP] | Japan | 4-195578 |
| Nov. 17, 1992 | [JP] | Japan | 4-306847 |

[51] Int. Cl.$^6$ .......................... G01N 27/26
[52] U.S. Cl. .......................... 204/415; 204/426; 204/431; 204/433; 204/403; 204/412; 204/418; 204/408; 435/817; 435/288
[58] Field of Search .............. 204/424, 426, 431, 412, 204/403, 415, 416, 418, 433, 435, 408; 435/288, 817

[56] References Cited

U.S. PATENT DOCUMENTS

| 4,139,833 | 2/1979 | Kirsch | 338/308 |
| 4,300,990 | 11/1981 | Maurer | 204/195 S |
| 4,368,453 | 1/1983 | Herden et al. | 338/25 |
| 4,418,329 | 11/1983 | Gruner | 338/28 |
| 4,437,970 | 3/1984 | Kitajima et al. | 204/412 |
| 4,516,106 | 5/1985 | Nolting et al. | 338/28 |
| 4,691,566 | 9/1987 | Aine | 73/204 |
| 4,888,463 | 12/1989 | Middlebrook | 219/201 |
| 4,888,988 | 12/1989 | Lee et al. | 73/204.26 |
| 4,975,175 | 12/1990 | Karube et al. | 204/412 |
| 5,010,315 | 4/1991 | Fedter et al. | 338/7 |
| 5,110,441 | 5/1992 | Kinlen | 204/418 |
| 5,172,332 | 12/1992 | Hungerford et al. | 364/510 |

FOREIGN PATENT DOCUMENTS

| 63-15484 | 1/1983 | Japan . |
| 63-164232 | 7/1988 | Japan . |
| 1-262679 | 10/1989 | Japan . |
| 2-263127 | 10/1990 | Japan . |
| 3-131003 | 6/1991 | Japan . |
| 3-204981 | 9/1991 | Japan . |

Primary Examiner—John Niebling
Assistant Examiner—Bruce F. Bell
Attorney, Agent, or Firm—Staas & Halsey

[57] ABSTRACT

A small oxygen electrode and a method of bonding a fluorine resin film are disclosed. This small oxygen electrode includes a flat electrode substrate having at least two electrodes (a working electrode and a counter electrode) formed thereon, and a container substrate having dents formed to confront the two electrodes and contain an electrolyte therein. The container substrate is bonded to the flat electrode substrate, so that the dent confronting the electrode constituting the working electrode has a through hole extending to the side opposite to the flat electrode substrate and a gas-permeable film is formed to cover the through hole. By using this dent structure, the preparation of an oxygen electrode can be conducted while maintaining a wafer form throughout the process, and formation of an electrode pattern can be facilitated. The method of bonding the fluorine resin film includes treating the fluorine resin film with an agent containing metallic sodium, then treating the fluorine resin film with a silane coupling agent. The treated fluorine resin film is fusion bonded by heating, and if necessary, conducting subsequent treatments in vacuo. By adopting this method, the fluorine resin film can be bonded tightly to the substrate and peeling of the fluorine resin film from the substrate can be prevented.

6 Claims, 27 Drawing Sheets

OXYGEN ELECTRODE AND TEMPERATURE SENSOR

CROSS REFERENCE TO RELATED APPLICATION

This application is a continuation-in-part of U.S. application Ser. No. 07/993,486, filed Dec. 17, 1992, now U.S. Pat. No. 5,358,619 which is a continuation-in-part of U.S. application Ser. No. 07/761,005, filed Sep. 17, 1991, now abandoned.

BACKGROUND OF THE INVENTION

1. Field of the Invention

The present invention relates to an oxygen electrode and a process for the preparation thereof. More particularly, the present invention relates to a small oxygen electrode fabricated by utilizing a micro-machining technique and a process for the preparation thereof. Furthermore, the present invention relates to a method of bonding a fluorine resin film onto a substrate. More particularly, the present invention relates to a method of bonding a fluorine resin film tightly to a silicon wafer, a glass substrate or the like in the field of the semiconductor process or micro-machining.

2. Description of the Related Art

Oxygen electrodes are advantageously used for the measurement of dissolved oxygen concentration. For example, the biochemical oxygen demand (BOD) in water is measured from the viewpoint of maintenance of the water quality. An oxygen electrode can be used as a device for measuring this dissolved oxygen concentration. Furthermore, in the fermentation industry, in order to advance the alcoholic fermentation at a high efficiency, it is necessary to adjust the dissolved oxygen concentration in a fermenter, and a small oxygen electrode can be used as means for measuring this dissolved oxygen concentration. Moreover, a small disposable oxygen sensor is demanded in the medical field. Still further, a small oxygen electrode can be combined with an enzyme to construct an enzyme electrode, and this enzyme electrode can be used for measuring the concentration of a saccharide or an alcohol. For example, glucose reacts with dissolved oxygen in the presence of an enzyme called glucose oxidase and is oxidized to gluconolactone. By utilizing the phenomenon that the amount of dissolved oxygen diffused in an oxygen electrode cell is reduced by this reaction, the glucose concentration can be determined from the amount of dissolved oxygen consumed.

As is seen from the foregoing description, the small oxygen electrode can be used in various fields such as environmental instrumentation, the fermentation industry and clinical medical treatment, especially in a case where the small oxygen electrode is attached to a catheter and is inserted into the body. Since the size is small and the electrode is disposable and cheap, the utility value is very high.

Since the size cannot be reduced in commercially available oxygen electrodes and mass production is impossible, the present inventors developed a new small oxygen electrode fabricated by a lithographic technique and an anisotropic etching technique and filed a patent application for this oxygen electrode (U.S. Pat. No. 4,975,175 corresponding to Japanese Unexamined Patent Publication No. 63-238548, see FIGS. 7 through 9). The oxygen electrode of this type has a structure in which two electrodes, that is, an anode 4 and a cathode 5, are formed on a hole 2 formed on a silicon substrate 1 by anisotropic etching through an insulating film 3. An electrolyte-containing liquid 6 is contained in this hole and finally, the top surface of the hole is covered with a gas-permeable (membrane) film 7. In the drawings, reference numeral 8 represents a responding part and reference numeral 9 represents a pad. This small oxygen electrode is small in size and the dispersion of characteristics is small. Moreover, since mass production is possible, the manufacturing cost is low.

Thus, conventional small oxygen electrodes have been improved almost to a practically applicable level by making improvements to the materials used for the fabrication. However, there are still some unsolved problems for preparing small oxygen electrodes along a manufacturing line and marketing them, as described below.

(1) In many cases, it is difficult to selectively form an electrolyte layer and a gas-permeable layer. Accordingly, the number of operations conducted for each chip is increased and the productivity is reduced. Therefore, the price of the small oxygen electrode rises.

(2) The operation of forming an electrode pattern from above the hole formed by anisotropic etching toward the bottom becomes difficult as the step depth increases, and the precision of formation of the pattern is reduced and special means such as lap baking becomes necessary. Accordingly, the fabrication is very troublesome.

(3) In conventional small oxygen electrodes, since the gas-permeable film is directly formed on the responding part, an electrode infiltrated into a gel or a polymeric solid electrolyte is used. However, it is difficult to regulate precisely the quantity of the electrolyte and, as a result, the dispersion of characteristics is adversely influenced.

(4) A gas-permeable film was formed at the outset by dip coating or spin coating a liquid material. Most of the materials used for such gas-permeable films (silicone resins and the like) deteriorate over time because the storage stability per year cannot be guaranteed.

(5) It is sufficient if the gas-permeable film is spread only in the vicinity of the working electrode, but in the above-mentioned oxygen electrode, where only one silicon substrate is used as the substrate, the gas-permeable film should also be formed in an irrelevant portion such as an anode region, and the gas-permeable film is readily damaged.

In the field of semiconductor processing or micro-machining, it is demanded that a fluorine resin film, for example, as a gas-permeable film or an insulating material, should be tightly bonded to a silicon wafer or a glass substrate, as in the case of a small Clark cell (barrier membrane type) fabricated by utilizing the micro-machining technique.

As previously pointed out, a small oxygen electrode can be used in the fields of environmental instrumentation, the fermentation industry and clinical medical treatment, especially in a case where the small oxygen electrode is attached to a catheter and is inserted into the body. Since the size is small and the electrode is disposable and cheap, the utility value is very high.

In the production of a small oxygen electrode, for example, a small oxygen electrode disclosed in U.S. Pat. No. 4,975,175 corresponding to Japanese Unexamined Patent Publication No. 63-238548, formation of a gas-permeable film is accomplished by forming a water-repellant polymer film by dip coating or spin coating, and in the latter case, bonding a fluorine type fluorinated ethylene propylene (FEP) film by heat fusion. The process disclosed in Japanese Unexamined Patent Publication No. 63-238548 is simple, but the process is defective in that it is generally difficult to reconcile the selective formation of a film pattern with an increase of the film strength.

In the conventional semiconductor process, there is known a method of bonding a fluorine resin as an insulating material to a silicon wafer or a glass substrate where fusion bonding is carried out at the fluorine resin-melting temperature (about 280° C.). However, the film formed by this method is readily peeled by incorporation of bubbles at the fusion bonding, change of the temperature or friction, and the resistance to wetting with water is very low.

In the case where a biosensor such as a small sensor is used in the medical field, the sensor should be subjected to high-pressure vapor sterilization in advance. Peeling of the gas-permeable film is frequently caused at this high-pressure vapor sterilization, and this is a very serious practical problem.

SUMMARY OF THE INVENTION

It is a primary object of the present invention to provide an oxygen electrode and a method of bonding a fluorine resin film, by which the foregoing problems can be solved.

In accordance with one aspect of the present invention, this object can be attained by an oxygen electrode comprising a flat electrode substrate having at least two electrodes (a working electrode and counter electrode) formed thereon, and a container substrate having dents formed to confront the two electrodes and contain an electrolyte therein, bonded to said flat electrode substrate, wherein of the dents, the dent confronting the electrode constituting the working electrode has a through hole extending to the side opposite to the flat electrode substrate and a gas-permeable film is formed to cover the through hole.

In accordance with another aspect of the present invention, there is provided a process for the preparation of an oxygen electrode, which comprises bonding a flat electrode substrate having at least two electrodes (a working electrode and a counter electrode) formed thereon to a container substrate having an electrolyte-injecting dent confronting the counter electrode and a through hole formed at the position confronting the working electrode, covering the through hole with a gas-permeable film to form a hole, and injecting an electrolyte into the dent and the hole.

In accordance with still another aspect of the present invention, there is provided a method of bonding a fluorine resin film which comprises treating the surface of the fluorine resin film with an agent containing metallic sodium, further treating the surface with a silane coupling agent, and fusion-bonding the treated fluorine resin film to a substrate by heating.

In accordance with a further aspect of the present invention, there is provided a method of bonding a fluorine resin film, which comprises treating the surface of a substrate with a silane coupling agent, and fusion-bonding the fluorine resin film to the treated surface by heating.

BRIEF DESCRIPTION OF THE DRAWINGS

The object as well as advantages of the present invention will become clear by the following description of preferred embodiments of the present invention with reference to the accompanying drawings, in which:

FIGS. 11A-11C are views showing the section of the oxygen electrode of FIG. 10, wherein FIG. 11A is a sectional view taken along a line A—A of FIG. 10, FIG. 11B is a sectional view taken along a line B—B and FIG. 11C is a sectional view taken along a line C—C;

FIGS. 12A-12D are explanatory views useful for explaining the fabrication process of the oxygen electrode shown in FIG. 11, wherein FIG. 12A shows a silicon wafer having an SiO₂ insulating film formed thereon after etching, FIG. 12B shows the state where an electrode sensitive portion is defined, FIG. 12C shows the state where a gas-permeable film is formed, and FIG. 12D shows the state where an electrolyte is filled into the sensitive portion;

DETAILED DESCRIPTION OF THE PREFERRED EMBODIMENTS

Figure 1:
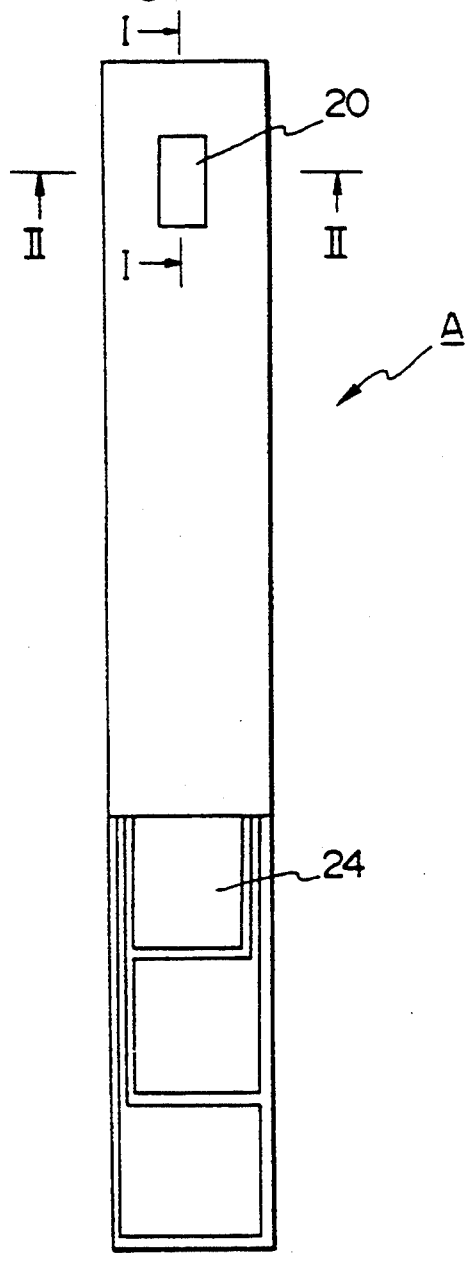
FIG. 1 is a plane view showing a small oxygen electrode according to one embodiment of the present invention.

As pointed out hereinabove, the size of the oxygen electrode is very small, and the basic technique of micro-machining is adopted for the preparation of this small oxygen electrode.

The process of the present invention utilizing this basic technique is characterized by the following features.

(1) Two substrates are used, and respective substrates are independently processed and bonded together to complete an oxygen electrode.

(2) The step of forming an electrolyte is omitted. Namely, the electrolyte is not charged by a manufacturer of the small oxygen electrode, but is injected by a user just before using.

(3) Electrode patterns of a working electrode, a reference electrode, a counter electrode and the like are formed with no deep steps, but they are formed on a substantially plane substrate.

(4) A through hole is formed only at a part of the working electrode and a gas-permeable film is coated only at this part.

(5) The gas-permeable film is bonded by heat fusion bonding or the like.

This oxygen electrode of the present invention can be fabricated by bonding the electrode substrate and the container substrate.

At least two electrodes, that is, a working electrode and a counter electrode, are formed on the flat electrode substrate.

In the case of a two-electrode structure, there are formed a cathode and an anode, and the cathode acts as the working electrode and the anode acts as the counter electrode.

The cathode and anode can be varied according to whether the electrode to be manufactured is of the polaro-type or the galvanize type. For example, in the production of an oxygen electrode of the polarographic, both the electrodes are constructed by gold electrodes or platinum electrodes, or an anode is constructed as the reference electrode, and a voltage is applied between both the electrodes at the measurement. In case of an oxygen electrode of the polarographic, a neutral aqueous solution such as a 0.1M aqueous solution of potassium chloride that hardly corrodes the silicon container portion is preferably used as the electrode. Furthermore, if an electrode of a metal more chemically reactive than gold or platinum, such as lead or silver, is used as the anode side electrode, an electrode of gold, platinum or the like is used as the cathode side electrode. In this case, an alkaline aqueous solution such as a 1M aqueous solution of potassium hydroxide is used as the electrolyte, and a galvanic oxygen electrode can be prepared.

In the case of a three-electrode structure, a reference electrode is further formed, and the working electrode and counter electrode are constructed by gold or platinum electrodes and a silver/silver chloride reference electrode or the like is preferably used as the reference electrode. These electrodes can be advantageously formed by such a film-forming method as vacuum evaporation deposition or sputtering.

Various solutions such as an aqueous solution of potassium chloride, an aqueous solution of potassium hydroxide and an aqueous solution of sodium sulfate can be used as the electrolyte.

It is indispensable that the gas-permeable film should be hydrophobic and should not allow permeation of an aqueous solution, and it also is important that the gas-permeable film should be bonded tightly with a good adhesion to a silicon substrate or a silicon oxide substrate by heat fusion bonding or the like. FEP and silicon varnish films can be preferably used as the gas-permeable film.

Preferred embodiments of the oxygen electrode of the present invention will now be described.

A reference electrode is formed on the flat electrode substrate in addition to a working electrode and a counter electrode, and a dent for injection of an electrolyte is formed on the container substrate.

The electrodes formed on the flat electrode substrate are preferably separated from one another to such an extent that they are not influenced by products formed on the surfaces of the respective electrodes.

As preferred examples of the material constituting the flat electrode substrate, there can be mentioned a Pyrex glass substrate, a lead glass substrate, a silicon substrate having a film of a Pyrex glass-containing borosilicate glass formed on the surface thereof, a silicon substrate having a lead glass film formed on the surface thereof, a glass substrate having a film of a Pyrex glass-containing borosilicate glass formed on the surface thereof, a glass substrate having a lead glass film formed on the surface thereof, and a silicon substrate having a thermally oxidized film on the surface thereof.

A pad is preferably formed at one end of each electrode formed on the electrode substrate, and the size of the pad is such that a socket terminal or the like of an IC can be used in the state directly gripped in the pad.

A semiconductor substrate, especially a silicon substrate, is advantageously used as the material of the container substrate. A (100) plane silicon substrate is especially preferably used as the silicon substrate.

When a silicon substrate is used, an insulating film can be constructed by a silicon oxide film or the like. For example, when the substrate is composed of silicon, a silicon oxide film can be easily formed by thermal oxidation of the substrate. A silicon nitride film has very good properties as the insulating film, but since anode junction (bonding) is impossible, the silicon nitride film cannot be used for the junction surface.

Furthermore, in the oxygen electrode of the present invention, it is preferred that the electrodes be formed in a shallow groove flatly etched in accordance with the electrode pattern.

Respective dents for containing the electrolyte, formed in the container substrate, can be connected to each other through a long groove.

On the front surface of the container substrate, that is, on the surface opposite to the surface to be bonded to the electrode substrate, a dent is formed in the peripheral edge portion of the through hole formed in the container substrate, and this dent is preferably covered with a gas-permeable film. If this structure is adopted, the distance between the gas-permeable film and the working electrode becomes much shorter and the sensitivity of the oxygen electrode per se can be improved.

A tetrafluoroethylene/hexafluoroethylene copolymer (FEP) film is preferably used as the gas-permeably film, and the thickness of this film is preferably smaller than 20 $\mu$m.

A gold electrode, a platinum electrode, a carbon electrode and the like are preferably used as the working electrode (cathode), and similarly, a gold electrode, a platinum electrode, carbon electrode and the like are preferably used as the counter electrode (anode). Furthermore, a silver/silver chloride electrode is preferably used as the reference electrode.

An aqueous solution of potassium chloride, an aqueous solution of potassium hydroxide and the like are preferably used as the electrolyte.

The small oxygen electrode of the present invention is used in the state where a certain voltage negative to the counter electrode (anode) or the reference electrode is applied to the working electrode (cathode). In the state where the responding part of this small oxygen electrode is immersed in a buffer solution, dissolved oxygen permeates through the gas-permeable film and arrives at the working electrode (cathode) where reduction is effected. If the value of a current generated at this point is measured, the dissolved oxygen can be known with the current value as a criterion.

The method of bonding a fluorine resin film according to the present invention will now be described in detail. As a result of research made with a view to solving the above-mentioned problems, the present inventors found that the problems can be solved by two means described below. The present invention has now been completed based on this finding.

According to the first means, the surface of a fluorine resin or the surface of a silicon wafer is chemically modified to form a chemical bond between them, whereby the bonding force is increased.

A fluorine resin is characterized in that it has no reactivity, but if only fluorine present in the surface portion is isolated and the surface is treated with a silane coupling agent, a chemical bond is formed between the fluorine resin and the silicon wafer, and tight bonding becomes possible.

Namely, the first means of the present invention is characterized in that the surface of a fluorine resin film is treated with an agent containing metallic sodium, the surface is then treated with a silane coupling agent and the treated fluorine resin film is fusion-bonded to a substrate by heating, or the surface of a substrate is treated with a silane coupling agent and a fluorine resin film is fusion-bonded to the treated substrate by heating. In the latter method, a fluorine resin film treated with an agent containing metallic sodium can be used as the fluorine resin film, or a fluorine resin film treated with an, agent containing metallic sodium and then treated with a silane coupling agent can be used as the fluorine resin film.

The second means is to cope especially with the latter problem described hereinbefore. It was found that at the fusion bonding of a fluorine resin film, air bubbles are left between the fluorine resin film and the substrate to reduce the bonding area between the film and substrate. At the high-pressure vapor sterilization, the bubbles are inflated to cause peeling of the film. It also was found that this problem of peeling can be solved by removing the air bubbles in vacuo or by carrying out the operation in vacuo throughout the fusion bonding.

The second means of the present invention is characterized in that the surface of a fluorine resin film is treated with an agent containing metallic sodium and is then treated with a silane coupling agent. The treated fluorine resin film is fusion-bonded to a substrate by heating. The fusion-bonded substrate is allowed to stand still in vacuo, and the fusion-bonded substrate is placed under atmospheric pressure and the substrate is fusion-bonded again. In addition, or alternatively, the surface of a fluorine resin film is treated with an agent containing metallic sodium and is then treated with a silane coupling agent, the treated fluorine resin film is fusion-bonded to a substrate in vacuo by heating, the fusion-bonded substrate is allowed to stand in vacuo and the fusion bonding is then carried out in vacuo again.

In the present invention, the term "substrate" means a silicon wafer, a glass substrate and the like, and the term "silane coupling agent" means silicon compounds such as $\tau$-APTES ($\tau$-aminopropyltriethoxysilane) and hexamethyldisilazane.

The present invention will now be described in detail with reference to the following examples that by no means limit the scope of the invention.

EXAMPLES

To begin with, one preferred example of the process for the preparation of a small oxygen electrode according to the present invention will be described with reference to FIGS. 1 through 4 of the accompanying drawings.

FIG. 1 is a plane view showing a small oxygen electrode A of the present invention.

Figure 2A:
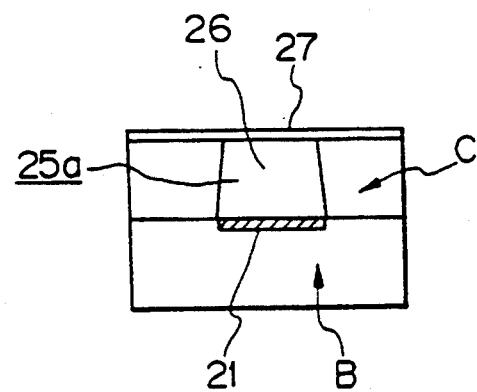
FIG. 2(A) is a cross-sectional view showing the section cut along line II—II in FIG. 1.
Figure 2B:
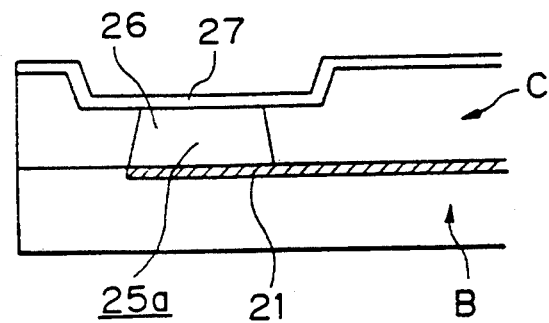
FIG. 2(B) is a cross-sectional view showing the section but along line I—I in FIG. 1.
Figure 3:
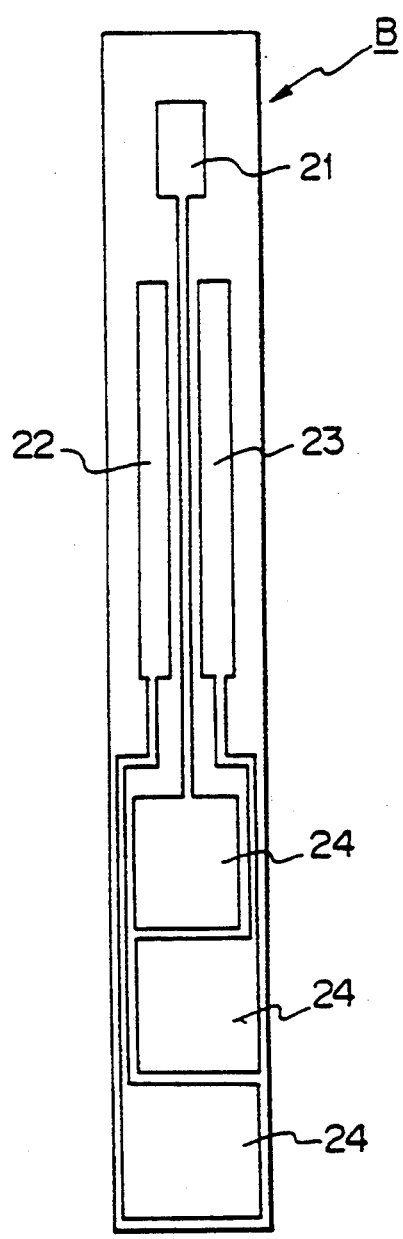
FIG. 3 is a plane view showing an electrode substrate constituting the oxygen electrode shown in FIG. 1.

Referring to FIGS. 1-4, the illustrated oxygen electrode has a rectangular shape, and a responding part (working electrode portion) is covered with a gas-permeable film 20. For connection to accessory devices, parts of a working electrode 21, a counter electrode 22 and a reference electrode 23 are exposed to form a pad 24 (FIG. 3). The illustrated electrode can have a two-electrode structure comprising only the working electrode 21 and counter electrode 22. Alternatively, a three-electrode structure further comprising the reference electrode 23 composed of a silver/silver chloride electrode can be adopted.

Figure 4:
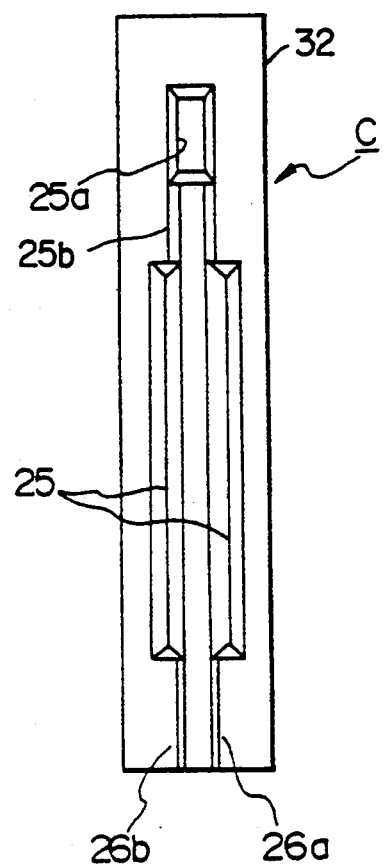
FIG. 4 is a plane view showing a container substrate constituting the oxygen electrode shown in FIG. 1.

The structure of the small oxygen electrode shown in FIG. 1 will be readily understood from FIGS. 3 and 4. More specifically, the working electrode 21, counter electrode 22 and reference electrode 23 are formed on an electrode substrate B composed of a glass. Dents 25 for storing electrolytes 26a and 26b are formed on a container substrate C at parts confronting the working electrode 21, counter electrode 22 and reference electrode 23, by anisotropic etching. The dent 25a at the part confronting the working electrode 21 is formed to pierce through a silicon substrate 32 to the opposite side for formation of a gas-permeable film 27 (FIG. 2(A)). Namely, the gas-permeable film 27 is formed on the top face of the dent 25a. Respective holes are connected to one another through fine grooves 25b. An electrolyte, for example, 0.1M KCl, is filled in the dents of the container substrate C after fabrication, and injection grooves 26a and 26b are formed in the vicinity of the pad 24 for injecting this electrolyte into fine holes.

The oxygen electrode A of the present invention is fabricated by bonding the electrode substrate B and the container substrate C together so that the electrodes formed on the electrode substrate B confront the dents formed in the container substrate C. FIG. 2A shows the section II—II of the so-fabricated oxygen electrode A.

The small oxygen electrode shown in FIG. 1 can be advantageously prepared according to the preparation process steps shown in sequence in FIG. 5. In the description given below, an embodiment where one oxygen electrode is formed for one wafer is explained to facilitate understanding, but it should be noted that practically, many small oxygen electrodes are simultaneously formed. In FIG. 5, only the vicinity of the working electrode is illustrated, but it should be noted that other portions are similarly formed.

I. Preparation of Electrode Substrate (1) A negative photoresist film having the same pattern as that of a working electrode (cathode), a counter electrode (anode) and a reference electrode, to be formed afterward, is formed on a so-called 2-inch Pyrex glass (Iwaki Glass 7740) substrate 30 in such a manner that the glass is exposed in electrode-forming areas.

(2) The same negative photoresist is coated on the entire back surface and baking is carried out at 150° for 30 minutes.

(3) A wafer is immersed for 1 hour in a mixed solution comprising 50% fluoric acid, concentrated nitric acid and 40% ammonium fluoride at a ratio of 1⅓ to etch the exposed glass. The etching depth is 3 $\mu$m.

Figure 5A:
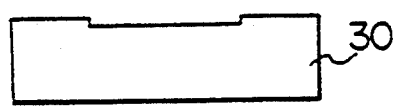
FIGS. 5A-5G are diagrams showing steps of the preparation of the oxygen electrode shown in FIG. 1 in regular sequence.

(4) The negative photoresist film formed through steps (1) and (2) is peeled in a mixed solution comprising sulfuric acid and hydrogen peroxide at a ratio of 2/1 (see FIG. 5A).

(5) The substrate 30 is sufficiently washed with a mixed solution of hydrogen peroxide and ammonia and then with pure water, and is then dried.

(6) A gold film is formed on the substrate by vacuum evaporation deposition. Since the adhesion between gold and glass is very poor, a thin chromium layer is interposed to improve the adhesion. The thickness of the chromium layer is 40 nm and the thickness of the gold layer is 400 nm.

(7) A positive photoresist film (OFPR-5000 supplied by Toyo Oka) is formed on the gold-deposited surface of the substrate.

(8) By using the same pattern as used at the step (1), a working electrode (cathode) pattern and a counter electrode (anode) pattern are formed.

(9) The resist pattern-formed substrate is immersed in a gold-etching solution formed by dissolving 4 g of KI and 1 g of I$_2$ in 40 ml of water to remove the exposed gold portion by etching. Then, the substrate is washed with pure water and the resist is removed by acetone.

(10) The substrate is immersed in a chromium-etching solution formed by dissolving 0.5 g of NaOH and 1 g of K$_3$Fe(CN)$_6$ in 4 ml of water to remove the exposed chromium portion.

(11) The substrate is sufficiently washed with pure water and is then dried.

In case of a two-electrode system comprising gold electrodes alone, the preparation terminates at the above step. However, in case of a three-electrode system, a reference electrode is further formed through the following steps.

(12) Silver is vacuum-deposited in a thickness of 400 nm on the substrate obtained at the step (11). In view of the adhesion, it is preferred that in the state of the step (11), the pattern of the gold electrode also be formed on the portion of the reference electrode. In the case where the gold pattern is located below, the Cr layer interposed at the step (6) becomes unnecessary.

(13) A positive photoresist is coated on the surface of the substrate, and after baking, light exposure and development, a photoresist pattern is formed only at a part where the reference electrode is to be formed.

(14) The entire substrate is immersed in a mixed solution comprising 29% ammonia, 31% hydrogen peroxide and pure water at a ratio of 11/20 to effect etching of silver.

(15) The substrate is sufficiently washed with pure water, and the entire substrate is immersed for 10 minutes in a 0.1M solution of FeCl$_3$ to form a thin layer of silver chloride on the surface of silver.

(16) The entire substrate is sufficiently washed with pure water.

Figure 5B:
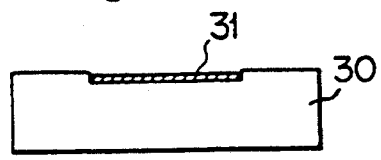

The electrode substrate is completed through the steps (1) to (16) (see FIG. 5B). Incidentally, in FIG. 5B, reference numeral 31 represents the working electrode (cathode).

II. Preparation of Container Substrate (1) A 2-inch (100) plane silicon wafer 32 having a thickness of 350 $\mu$m is prepared, and the wafer is washed with a mixed solution of hydrogen peroxide and ammonia and with concentrated nitric acid.

(2) The silicon wafer 32 is subjected to wet thermal oxidation at 1050° C. for 200 minutes to form an SiO$_2$ film 33 having a thickness of 1.0 $\mu$m on the entire surface.

(3) A negative photoresist (OMR-83 supplied by Tokyo Oka) having a viscosity of 60 cP is coated on the smooth surface of the silicon substrate, and light exposure, development and rinsing are carried out to form a resist pattern for etching on the wafer.

Figure 5C:
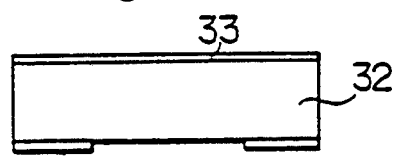

(4) The wafer is immersed in a mixed solution comprising 50% fluoric acid and 40% ammonium fluoride at a ratio of 1/6 to etch the exposed SiO$_2$ portion (see FIG. 5C).

(5) The negative photoresist film formed through the steps (1) and (2) is peeled in a mixed solution comprising sulfuric acid and hydrogen peroxide at a ratio of 2/1.

(6) The substrate is immersed in 35% KOH maintained at 80° C. to effect anisotropic etching of silicon and form dents corresponding to the electrode patterns prepared in the process (I). When the dent patterns are complicated, the steps (1) through (6) are repeated a number of times. Finally, a container substrate having electrolyte-storing cavities in the portions confronting the counter electrode and reference electrode and a through hole 34 in the portion confronting the working electrode is obtained.

(7) If $SiO_2$ used as the mask is left on the surface on the silicon, since a higher temperature is necessary for the anode bonding (III) described below, $SiO_2$ is completely removed in the etching solution used at the step (4).

Figure 5D:
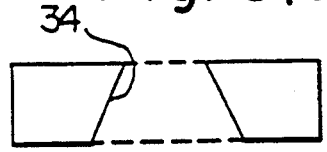

The electrolyte-storing container substrate is completed through the steps (1) to (7) (see FIG. 5D).

III. Bonding of Electrode Substrate and Container Substrate (1) The electrode substrate completed by the process (I) is subjected to ultrasonic washing in pure water, and the electrolyte-storing container substrate completed by the process (11) is sufficiently washed with an aqueous solution of hydrogen peroxide/ammonia and with pure water.

(2) Registration of the pattern of the electrode-forming surface, obtained in the process (I), with the pattern of the surface having dents formed thereon by etching in the process (11) is carried out in a clean atmosphere.

Figure 5E:
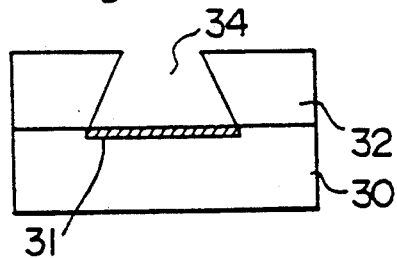

(3) A voltage of 1200 V is applied between the substrates at a temperature of 250° C. to effect anodic bonding between the electrode substrate and the container substrate, so that the electrode substrate is located on the negative side (see FIG. 5E).

IV. Formation of Gas-Permeable Film (1) A gas-permeable film (for example, FEP film having a thickness of 12 $\mu$m (supplied by Toray)) is cut in an appropriate size on the surface, opposite to the bonded surface, of the container substrate prepared by the process (11) in the portion where the through hole is formed.

Figure 5F:
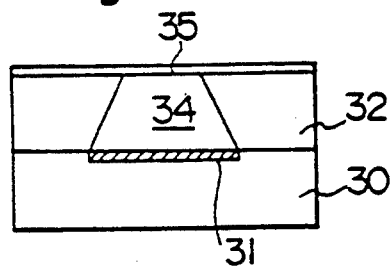

(2) The substrate which has passed through the step (1) is heated at a temperature where FEP melts, whereby the FEP film 35 is bonded to the substrate (see FIG. 5F).

V. Cut-Out of Substrate (1) The substrate having many oxygen electrodes formed thereon is cut out into chips by a dicing saw.

VI. Injection of Electrolyte

When the size of holes formed within the small oxygen electrode is small, injection of the electrolyte 36 can be accomplished by immersing the small oxygen electrode in 0.1M KCl and placing the entire electrolyte under a reduced pressure. If injection is difficult by this method, the following operation is carried out to facilitate the injection.

(1) The electrolyte is charged in a beaker, and the portion of the electrolyte-injecting groove of the small oxygen electrode is placed in the electrolyte and the portion of the gas-permeable film is placed in the gas phase. In this state, the electrolyte and the beaker are charged in the sealed container and deaeration is carried out by a vacuum pump.

(2) After the container has been allowed to stand still for a while, air is abruptly introduced into the container substrate. By this operation, the electrolyte 36 is introduced at a time to the point where the gas-permeable film is present.

(3) In the case wherein bubbles are left in the portion of the gas-permeable film, the above operations (1) and (2) are repeated.

For injection of the electrolyte, there can also be adopted a method in which sodium alginate containing the electrolyte is charged in the dents and through hole of the oxygen electrode, the entire oxygen electrode is immersed in an aqueous solution of calcium chloride to fill the aqueous solution into the dents and through hole and to gel sodium alginate to calcium alginate, and the oxygen electrode is immersed in the above aqueous solution of the electrolyte, whereby the electrolyte is sufficiently filled into the oxygen electrode. If the dents are too long to gel the sodium alginate in a short time, the procedure can be reversed. Namely, the dents and through hole are first charged with calcium chloride solution, the entire electrode is baked to evaporate water in the solution, and then sodium alginate solution containing the electrolyte is charged into the cavity to obtain the gel. Alternatively, the oxygen electrode is immersed in a fused agarose gel containing the electrolyte, and the gel can be introduced into the dents and through hole in the interior of the oxygen electrode.

Figure 5G:
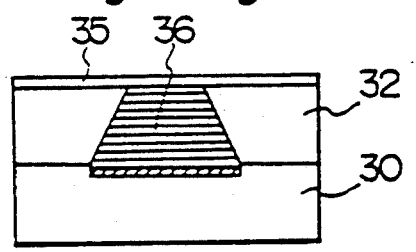

After these operations, a small oxygen electrode capable of practically working can be provided (see FIG. 5G).

VII. Connection to External Meters

When the thus fabricated small oxygen electrode is used, it is necessary to connect the small oxygen electrode to an exterior amplifier or detector. If a large pad portion is formed as shown in FIG. 1, for example, a fitting portion of an IC socket is taken out, a lead line is attached thereto and the connection is effected through the lead line. In the case where it is apprehended that also the pad portion may be immersed in the solution, a lead line (for example, an aluminum line having a diameter of about 50 $\mu$) is bonded to the pad portion, and the pad portion and the lead line portion are insulated with a resin. In the case where a problem arises as regards the bonding strength, there can be adopted a method in which even the pad portion is covered with the container substrate (silicon), a through hole is formed in the pad portion as well as in the responding portion, the top end of the lead line is inserted into the pad portion, and the inserted lead line is fixed with an indium or silver paste and further fixed with an insulating resin.

VIII. Example of Use of Small Oxygen Electrode

Figure 6:
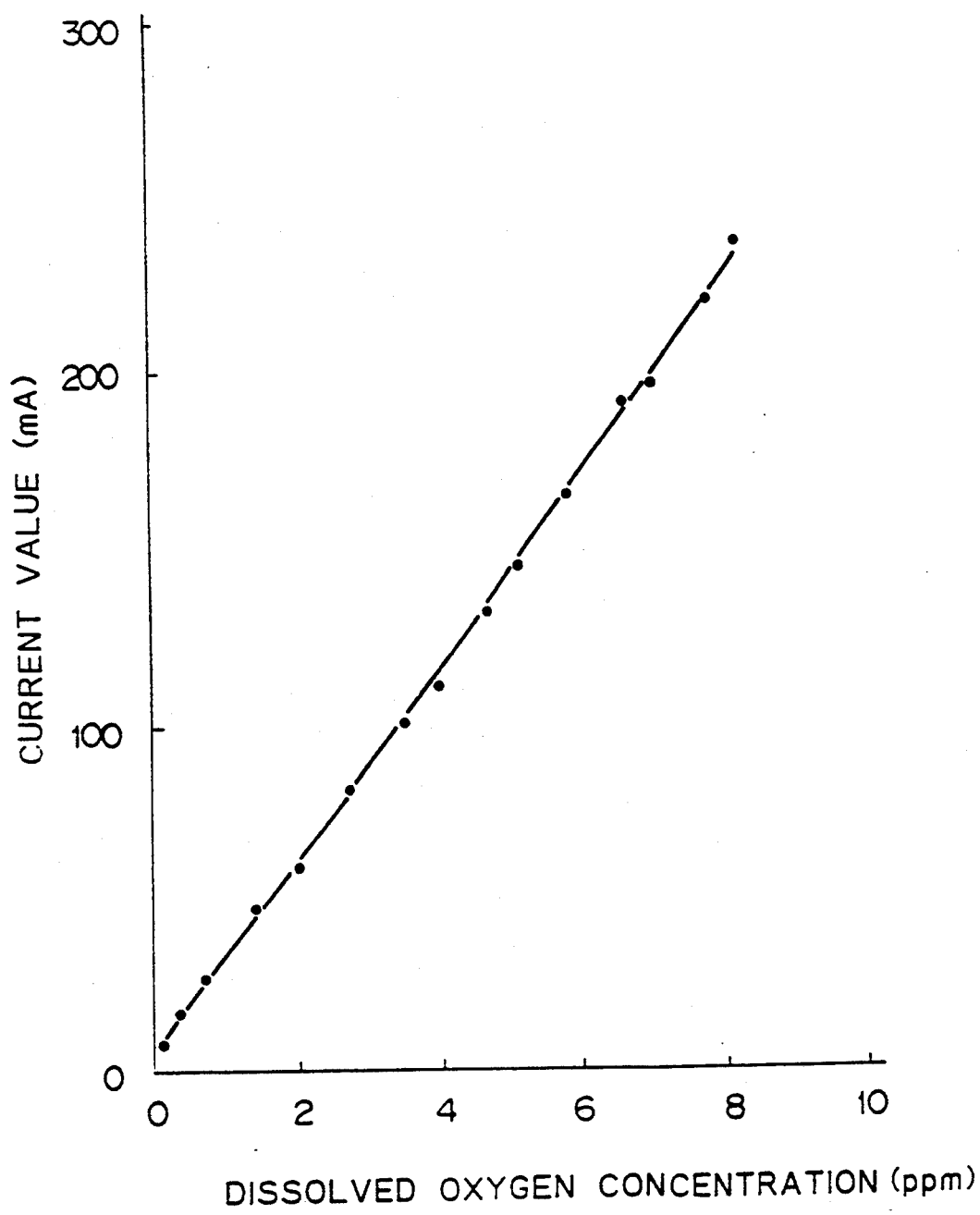
FIG. 6 is a graph showing a calibration curve of the small oxygen electrode of the present invention.
Figure 7:
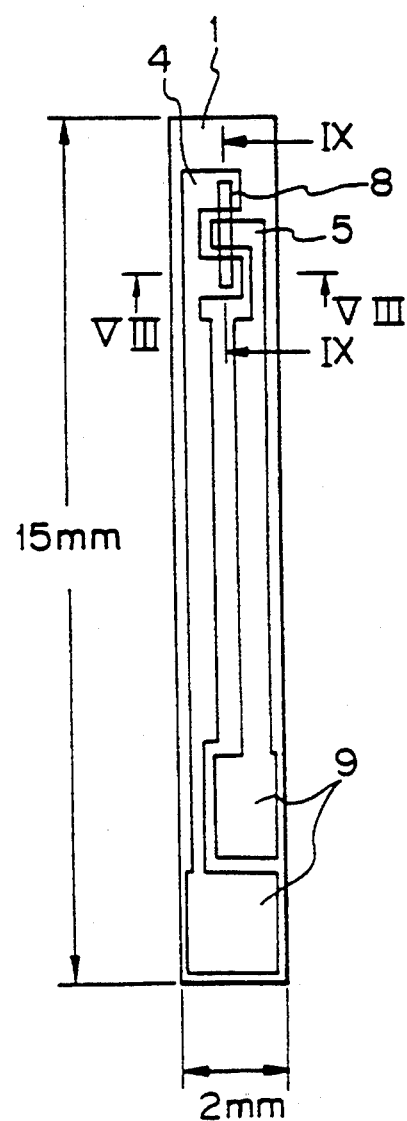
FIG. 7 is a plane view showing a conventional oxygen electrode.
Figure 8:
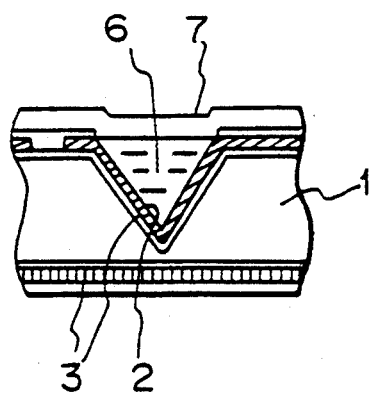
FIG. 8 is a cross-sectional view showing the section taken along line VIII—VIII in the oxygen electrode shown in FIG. 7.
Figure 9:
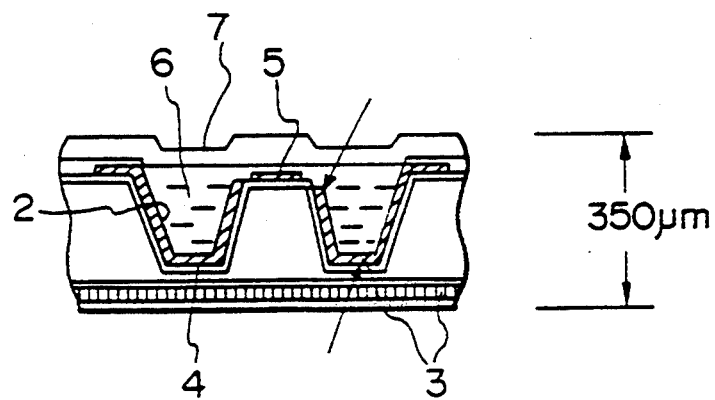
FIG. 9 is a cross-sectional view showing the section taken along line IX—IX in the oxygen electrode shown in FIG. 7.

The characteristics of the above-mentioned small oxygen electrode are examined at 25° C. in a 10 mM phosphate buffer solution having a pH value of 7.0. The applied voltage is $-0.8$ V (vs. Ag/AgCl). As compared with the case of direct injection of a 0.1M KCl electrolyte into the electrode, use of the electrolyte in the state filled in a calcium alginate gel is advantageous, because a stable output is obtained with reduced noise. The 90% responding time is about 2 minutes, and in the state where the dissolved oxygen concentration is 0%, the residual current value is about 7%. The obtained calibration curve is shown in FIG. 6. The dissolved oxygen concentration is lower than 8.2 ppm (the saturation concentration of dissolved oxygen) and a good linearity is observed.

Since the process of the present invention has the above-mentioned structure, the step of forming an electrolyte layer can be omitted. Accordingly, an oxygen electrode can be prepared while maintaining a wafer form throughout the process without any particular trouble, and therefore, an effect of reducing the manufacturing cost can be attained. Moreover, since electrodes are formed on a flat surface having no deep hole, an electrode pattern can be easily formed. Furthermore, since the electrode can be stored in the dry state free of an electrolyte layer, deterioration of a gas-permeable film is hardly caused. Accordingly, long-prior storage is possible and an area for which the gas-permeable film is necessary is considerably restricted, and therefore, the gas-permeable film is hardly damaged. Still further, since a large quantity of the electrolyte can be stored, the life of the electrode can be prolonged.

The method of bonding a fluorine resin film according to the present invention will be described with reference to the following examples.

Example A

An FEP (fluoroethylene-propylene supplied by Toray) film having a thickness of 12 μm was used as the fluorine resin film. The FEP film was washed with ethanol and dried (first step). The washed sample was immersed for 30 seconds in an agent containing Na (Chemgrip supplied by Norton) to effect reaction, and the sample was washed with acetone three times (second step). Then, the sample was immersed for 30 minutes in a 10% aqueous solution of τ-APTES (silane coupling agent composed of τ-aminopropyltriethoxysilane supplied by Aldrich) at 50° C. to effect reaction (third step).

Samples obtained at the respective steps are prepared.

A silicon wafer was used as the substrate, and the untreated silicon wafer (a) and the silicon (b) treated with the silane coupling agent (τ-APTES) were prepared.

The samples obtained at the respective steps were independently placed on the two wafers (a) and (b), and fusion bonding was carried out on a hot plate maintained at 280° C. Then, in an autoclave, high-pressure sterilization was carried out in water at 120° C. under 2 atmospheres for 15 minutes, and the fusion bonding state was examined.

The bonding ratio after the sterilization is shown in Table 1. With respect to each sample, 10 test pieces were tested. According to the conventional method ((1)-(a)), the film was readily peeled in water. None of the surface-treated samples, other than the sample (2)-(a), were peeled in water, and strong bonding was attained in these samples. Especially, the sample (2)-(b) had a strong bonding force and showed a high resistance in an adhesive cellophane tape peeling test.

TABLE 1

Surface Treatment Conditions and Bonding Ratio (%)

| Fluorine Resin (Si Wafer) | Sample (1) at First Step (untreated) | Sample (2) at Second Step (Na agent) | Sample (3) at Third Step (Na Agent & τ-APTES) |
|---|---|---|---|
| (a) Untreated | 0 | 0 | 100 |
| (b) τ-APTES | 100 | 100 | 100 |

Note
: very strong

Example B

A substrate having a sensor proper, such as a small oxygen electrode, formed thereon was sufficiently subjected to ultrasonic washing in pure water. Than, an FEP (supplied by Toray) film having a thickness of 12 μm was immersed in a metallic sodium-containing treating agent (for example, Chemgrip) to remove fluorine atoms present on the film surface. Then, the FEP film was further treated with a silane coupling agent (τ-APTES).

The surface-treated film was placed on the substrate heated at 270° C. to effect fusion bonding. In order to remove bubbles left between the film and the substrate, the substrate to Which the film has been fusion-bonded was placed in a vacuum for 5 minutes and immediately, the pressure was returned to atmospheric pressure, and the film-bonded substrate was heated at 270° C. again. This heating operation was repeated as needed. Thus, the adhesion of the film was improved.

In the case where the film is fusion-bonded to a flat substrate, a sufficient strength can be obtained using only the treatment with an agent containing metallic sodium and a silane coupling agent. However, in the case where the film is bonded to a substrate having convexities and concavities on the surface, such as a small practical oxygen electrode, bubbles are often left between the film and the substrate. It is conceivable that such bubbles may be inflated during the high-pressure vapor sterilization treatment to cause peeling of the film, because the contact area between the film and the substrate is reduced and the adhesion is degraded. In this case, a vacuum treatment during the fusion bonding of the film is effective.

The effects attained by the method of Example B are shown in Table 2.

The film treated with metallic sodium and τ-APTES as described in Example B was fusion-bonded to an untreated silicon wafer, and the vacuum treatment was carried out to complete a small oxygen electrode. Separately, the film treated with an agent containing metallic sodium and τ-APTES was fusion-bonded to an untreated silicon wafer, but the vacuum treatment was not carried out. The obtained small oxygen electrode was used as a comparative electrode. The two electrodes were subjected to the high-pressure vapor sterilization and then, the states of the films were examined and compared. The obtained results are shown in Table 2.

TABLE 2

Effect by Vacuum Treatment at Fusion Bonding

| | Film Peel Ratio (%) |
|---|---|
| Untreated Sample | 75 |
| Vacuum-Treated Sample | 0 |

From the results shown in Table 2, it is confirmed that a high effect can be attained by the vacuum treatment.

As is apparent from the foregoing description, according to the present invention, by using the above-mentioned dent structure, the substrate and the film can be tightly bonded to each other, and peeling of the fluorine resin film from the substrate can be prevented. Especially, in the case where a practical oxygen electrode is once prepared and is then subjected to a severe treatment such as the high-pressure vapor sterilization, according to the method of the present invention including the vacuum treatment, the adhesion of the gas-permeable film is highly improved, and peeling of the film is not caused. Thus, excellent effects can be attained according to the present invention.

Next, a preferred embodiment of the oxygen electrode according to the present invention and its production method will be explained with reference to the accompanying drawings.

Figure 10:
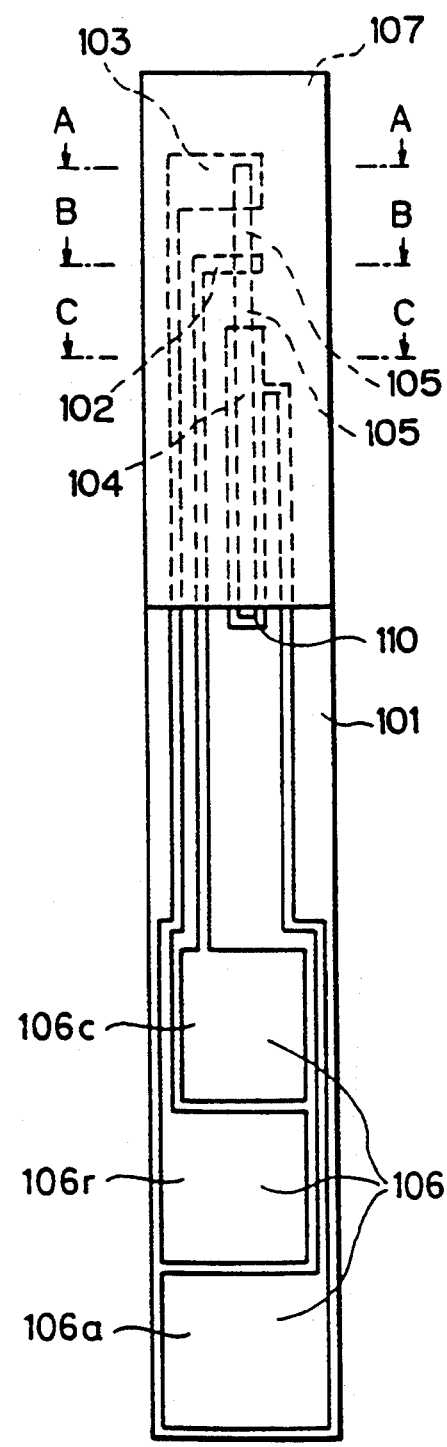
FIG. 10 is a plan view showing an example of the oxygen electrode according to the present invention.
Figure 11A:
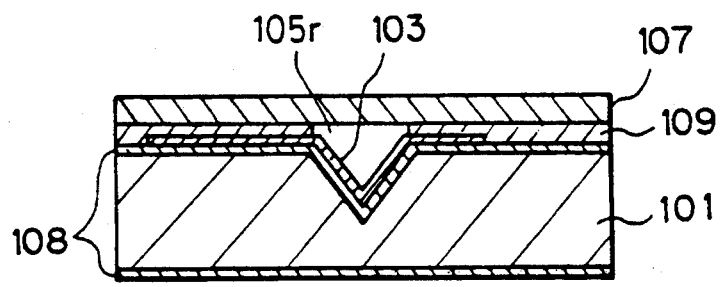
Figure 11B:
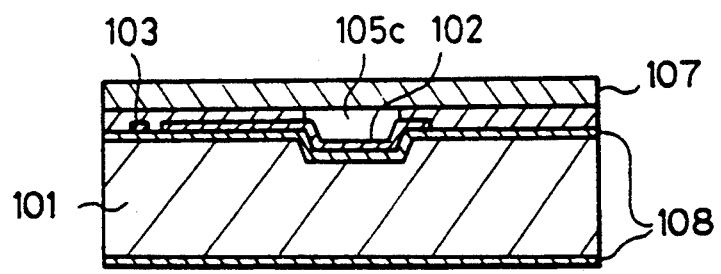
Figure 11C:
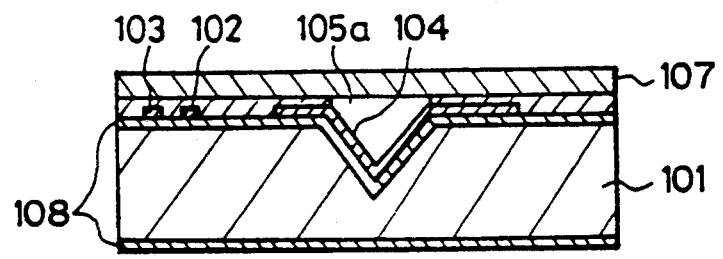

FIG. 10 is a plan view showing a preferred embodiment of the oxygen electrode of the present invention, and FIG. 11 is a sectional view of a sensitive portion of the oxygen electrode. FIG. 11A is a sectional view taken along a line A—A of FIG. 10, FIG. 11B is a sectional view taken along a line B—B of FIG. 10 and FIG. 11C is a sectional view taken along a line C—C of FIG. 10. The oxygen electrode shown in these drawings has a rectangular shape, and a silicon substrate 101 has a dent 105 (105a, 105c, 105r) (corresponding to the sensitive portion of the oxygen electrode) formed by anisotropic etching. The depth of the dept portion 105C where the working electrode (cathode) is to be formed is different from the depth of the dent portions 105a or 105r where the counter electrode (anode) or the reference electrode is to be formed respectively. A working electrode 102, a reference electrode 103 and a counter electrode 104 are formed in each of the dent portion 105c, 105r and 105c respectively of the dent 105. The working electrode 102 is made of silver, the reference electrode 103 is made of silver/silver chloride, and the counter electrode 104 is made of gold. A gas-permeable film 107 is formed at the upper part of the dent 105 other than the portion of a through-hole 110. After this oxygen electrode is completed, 0.1M KCl aqueous solution as an electrolyte is filled into the dent 105 of the silicon substrate 101. A part of each of these electrodes 102, 103, 104 is extended outside from the dent 105 and forms a pad 106 on the surface of the substrate 101.

The oxygen electrode shown in these drawings can advantageously be produced in accordance with a production process which will be illustrated sequentially in FIG. 12. To have the present invention more easily understood, the following explanation will be given on the case where only one oxygen electrode is formed on one silicon wafer. It is to be noted, however, that a large number of oxygen electrodes are formed simultaneously in practice.

(1) Wafer washing

A 3-in. diameter (100) plane silicon wafer 101 was prepared, and was washed with a mixed solution of hydrogen peroxide and ammonia, and then with concentrated nitric acid.

(2) Formation of SiO$_2$ film

The silicon wafer was thermally oxidized while wet, and a 1.0 μm-thick SiO$_2$ film was formed on the entire surface of the silicon wafer 101.

(3) Formation of etching pattern

A negative type photoresist ("OMR-83" (trade name), a product of Tokyo Oka K. K., viscosity=100 cps) was coated to a surface of the substrate, and then exposure, development and rinsing were carried out to form a resist pattern for etching on the wafer.

(4) Baking of substrate

After the same negative type photoresist as the one used above was also coated to the back of the substrate, the substrate was baked at 150° C. in the course of 30 minutes.

(5) Etching of SiO$_2$ film

The wafer was immersed in a 1:6 aqueous mixed solution of 50% hydrofluoric acid and 40% ammonium fluoride, and SiO$_2$ of exposed portions not covered with the photoresist was removed by etching. Subsequently, the resist was removed by a sulfuric acid/hydrogen peroxide (2:1) solution.

(6) Anisotropic etching of Si

Anisotropic etching of silicon was carried out in a 35% aqueous potassium hydroxide solution at 80° C.. In this case, etching was suspended at an intermediate stage in order to make the depth of the formation portion 105c of the working electrode 102 shallow or smaller than that of the formation portions 105a, 105r of the counter and reference electrodes 104, 103 as shown in FIG. 11. After the steps (1) to (5) were repeated once again, etching of the formation portions 105a, 105r of the counter and reference electrodes 104,103 were carried out. The depth of the working electrode formation portion 105c was 20 μm and that of the counter and reference electrode formation portions 105a, 105r was 150 μm. Thereby, the mutual diffusion of a precursor, such as an intermediate material OH$^-$ formed on the cathode by the reaction: $O_2+2H_2O+4e \rightarrow 4OH^-$, or, a water soluble complex formed on the Ag anode by the reaction:

complex, to the other electrode, particularly the diffusion or flow of the precursor formed on the anode to the reference electrode can be effectively limited or prevented by the shallow depth working electrode formation portion 105c of the dent 105. On the same reason, the distances of each of the electrodes are adjusted so that such mutual, diffusion or flow can be prevented.

(7) Formation of SiO$_2$ layer

Figure 12A:
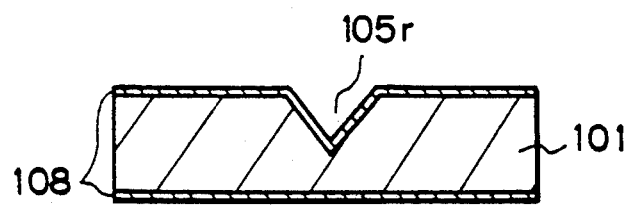

After the substrate was washed, a 1 μm-thick SiO$_2$ layer (insulating layer) 108 was again formed by thermal oxidation. FIG. 12A shows the section of the substrate 101 (corresponding to the reference electrode formation portion 105r) after the treatment was carried out up to this stage.

(8) Formation of chromium and gold thin film

A chromium thin film (400 Å, for the adhesion between gold and the substrate) and then a thin gold film (4,000 Å) were formed on the etched surface of the wafer 101 by vacuum deposition.

(9) Formation of resist pattern for counter electrode

A resist pattern for forming the counter electrode 104 was formed on the thin gold film of the wafer by the use of a positive type photoresist ("OFPR-5000",) trade name, a product of Tokyo Oka K. K., viscosity=50 cps).

(10) Etching of gold

The substrate having the resist pattern thus formed thereon was immersed in a gold etching solution prepared by dissolving 4 g of KI and 1 g of I$_2$ in 40 ml of water, and the exposed gold portions were removed by etching. After the substrate was further washed with pure water, the resist was removed by acetone.

(11) Etching of chromium

Next, the substrate was immersed in a chromium etching solution prepared by dissolving 0.5 g of NaOH and 1 g of $K_3Fe(CN)_6$ in 4 ml of water, and the exposed chromium layer was removed.

(12) Formation of silver thin film

After the substrate having the gold pattern 104, 106a thus formed thereon was sufficiently washed, a thin silver film (4,000 Å) was formed by vacuum deposition. The counter electrode 104 was covered and protected during this vacuum deposition lest silver adhered to the counter electrode.

(13) Formation of working & reference electrode pattern

A photoresist pattern for the working electrode 102 and the reference electrode 103 was formed in the same way as in (9).

(14) Etching of silver

The substrate having the resist pattern formed thereon was immersed in an etching solution for silver which was a 1:1:20 solution of 29% aqueous ammonia, 31% hydrogen peroxide solution and pure water, and the exposed silver portions were removed by etching. Furthermore, after the substrate was washed with pure water, the resist was removed by acetone.

(15) Definition of electrode sensitive portion

Figure 12B:
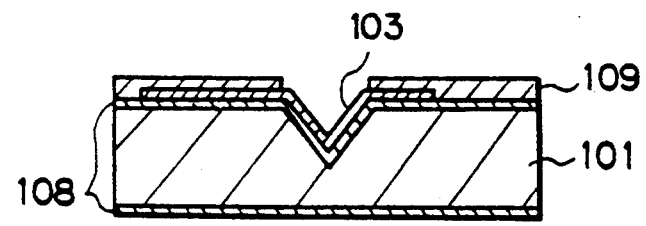

Portions other than the portion at which the oxygen electrode was to be formed (the electrode sensitive portion, that is, the portion anisotropically etched) and other than the pad portion 106, were covered with a negative type photoresist 109 ("OMR-83", viscosity=100 cps) (film thickness =2.8 μm). FIG. 12B shows the section of the substrate after the treatment described above so far was carried out.

(16) Formation of gas-permeable film

Figure 12C:
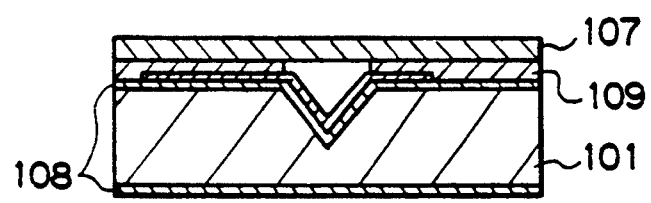

An FEP film 107 (a product of Toray Co., film thickness=12 μm) was applied by thermal fusing onto the sensitive portion except for the portion of the through-hole 110 as shown in FIG. 10. The temperature at this time was 280° C. FIG. 12C shows the section of the substrate for which the treatment described so far was carried out.

(17) Cut-out of substrates

A large number of oxygen electrodes formed on the substrate were cut out into the chip form by the use of a dicing saw.

(18) Changing of electrolyte

Figure 12D:
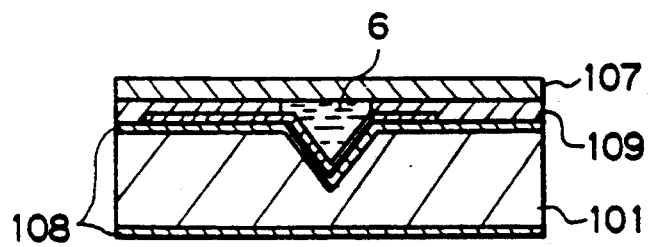

The main body of the oxygen electrode was dipped into 0.1M KCl aqoues solution placed into a beaker, and each beaker was exposed to a reduced pressure so that the electrolyte 6 was filled or charged into the sensitive portion from an open hole portion 110 (FIG. 12D). After this open hole portion 110 was closed by a vinyl tape, each oxygen electrode functioning was thus practically obtained.

The oxygen electrode completed in this manner operates by measuring a reduction current of oxygen generated from the working electrode 102 under the state where the sensitive portion is dipped into a buffer solution and a predetermined voltage is applied across the working electrode 102 and the reference electrode 103 (for example, with the application of −0.6 V to the working electrode with respect to the Ag/AgCl reference electrode). Apropos of this, the silver/silver chloride reference electrode can be formed by applying −0.6 V for 30 seconds to the working electrode 102, for example, before the start of use.

According to the present invention, the oxygen electrode which is simple both structurally and from the aspect of the production process can be obtained because the dent 105 for filling the electrolyte solution 6 and each electrode 102, 103, 104 constituting the oxygen electrode are formed on the same substrate. A mass-production of the oxygen electrodes becomes possible by employing a silicon wafer substrate, or the like.

Furthermore, since the oxygen electrode can be preserved under the dry state not containing the electrolyte, degradation of the electrode and the gas-permeable film which would otherwise be affected easily by the electrolyte does not occur so easily, and preservation for an extended period becomes possible.

Hereinafter, a biosensor and a biosensor assembly according to embodiments of the present invention will be explained with reference to the drawings.

First Embodiment. (L-glutamic acid sensor)

Figure 13:
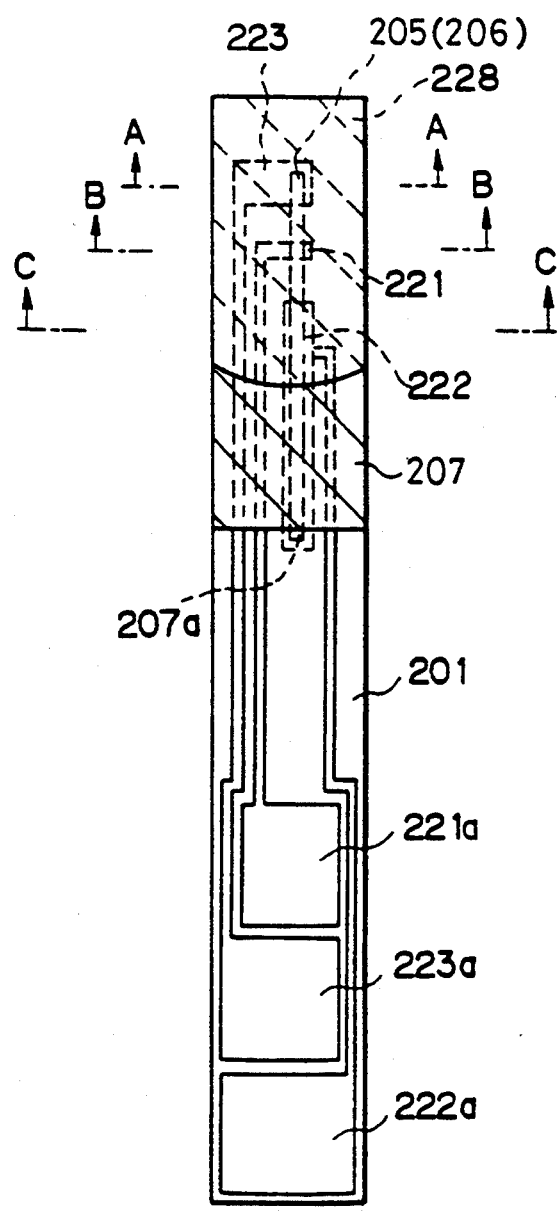
FIG. 13 is a plan view of biosensor for L-glutamic acid according to the embodiment of the present invention.

Refer to FIGS. 13 and 14.

FIG. 13 is a plan view of a biosensor for L-glutamic acid according to an embodiment of the present invention. A rectangular dent 205 is formed on one of the surfaces of a substrate 201 consisting of a silicon sheet member having a shape of a rectangle of 15 mm×2 mm×0.4 mm, and the surface of both of the substrate 201 and the dent 205 is covered with an insulating film 201a. Two or three electrodes are formed on this insulating film 201a. In this embodiment, the electrodes 202 consist of a working electrode 221 made of silver, a counter electrode 222 made of gold and a reference electrode 223 made of silver/silver chloride. The principal portions of the dent 205 and the electrodes 202 are covered with a gas-permeable film 207 made of fluorinated ethylene propylene, and an electrolyte consisting of 0.1M KCl aqueous solution is filled into the dent 205. Reference numerals 221a, 222a and 223a denote connecting pads of the working electrode 221, counter electrode 222 and reference electrode 223, respectively. Reference numeral 207a denotes a through-hole for injecting the electrolyte 206, and reference numeral 208 denotes an enzyme- or microorganism-immobilizing film to which L-glutamic oxidase acid is immobilized.

Figure 14A:
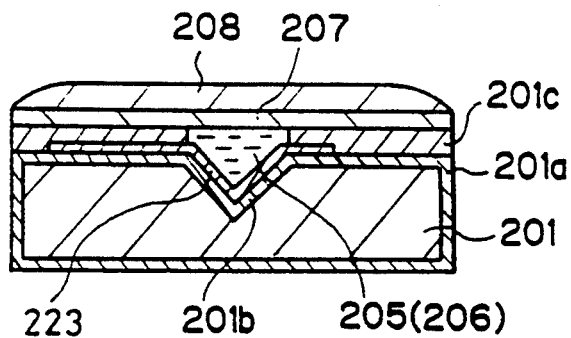
FIGS. 14A-14C are sectional views of the biosensor for L-glutamic acid shown in FIG. 13 taken along a line A—A, a sectional view taken along a line B—B and a sectional view taken along a line C—C of FIG. 13.
Figure 14B:
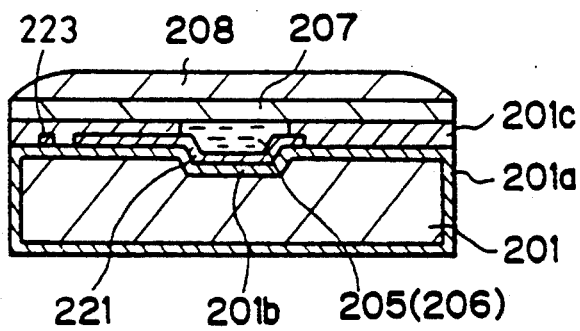
Figure 14C:
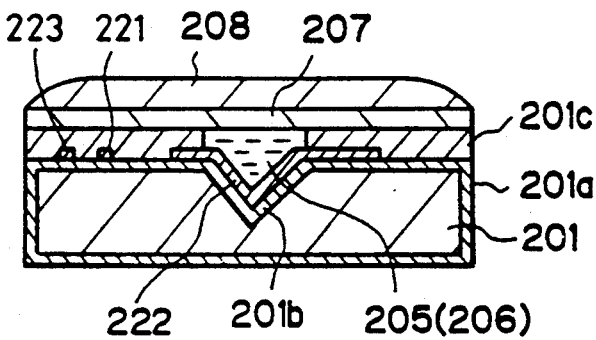

Refer to FIGS. 14A, 14B and 14C.

FIGS. 14A, 14B and 14C are a sectional view taken along a line A—A of the plan view shown in FIG. 14 (a sectional side view corresponding to the reference electrode 223), a sectional view taken along a line B—B (a sectional side view corresponding to the working electrode 221) and a sectional view taken along a line C—C (a sectional side view corresponding to the counter electrode 222), respectively. The reason why only the dent 205 corresponding to the working electrode 221 is shaped in a small depth is that if the reference electrode 223 is provided in addition to the working electrode 221 and the counter electrode 222, it becomes possible to prevent the product generated on the counter electrode 222 from flowing into the reference electrode 223 side (and vice versa), and this arrangement is desirable from the aspect of performance of the oxygen electrode.

Next, the production process will be explained.

Figure 15A:
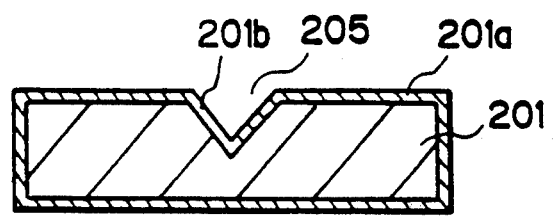
FIGS. 15A—15C are sectional views showing step-wise the pre-stage (production process of an oxygen electrode) of the production process of the biosensor for glutamic acid according to the present invention.

Refer to FIG. 15A.

a) The silicon substrate 201 is washed with a mixed aqueous solution of hydrogen peroxide solution and aqueous ammonia and then with concentrated nitric acid.

b) The substrate is wet oxidized, and a 1.0 μm-thick silicon dioxide film 201a is formed on the entire surface of the substrate 201.

c) A negative type photoresist ("OMR-83", a trade name, a product of Tokyo Oka K.K.) is spin-coated. After exposure is carried out using a mask (not shown) having the shape of the dent 205, development is carried out so as to form a resist mask (not shown) for forming the dent.

d) The silicon dioxide film 201a is etched using this resist mask (not shown) and a mixed aqueous solution of hydrofluoric acid and ammonium fluoride as an etchant.

e) The silicon substrate 201 is etched anisotropically to form the dent 205 using the etched silicon dioxide film 201a as the mask and an aqueous potassium hydroxide solution as the etchant.

f) A 1 μm-thick silicon dioxide film 201b is deposited on the inner surface of the dent 205 thus etched anisotropically. This step can be carried out easily by oxidation.

Figure 15B:
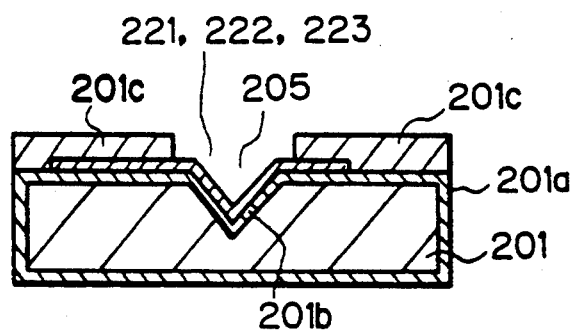

Refer to FIG. 15B.

g) A 400 Å-thick chromium film (not shown) and a 4,000 Å-thick gold film (not shown) are formed.

h) A positive type resist ("OFPR-5000", trade name, a product of Tokyo Oka K.K.) is spin-coated, and a resist mask (not shown) for forming the counter electrode 222 is so formed as to remain only on a counter electrode formation region.

i) The counter electrode 222 is formed using a gold etching solution (an aqueous solution prepared by dissolving 4 g of potassium iodide and 1 g of iodine in 40 ml of water) and a chromium etching solution (an aqueous solution prepared by dissolving 0.5 g of sodium hydroxide and 1 g of potassium ferricyanide in 4 ml of water).

j) After the counter electrode 222 is covered with a photoresist, a 4,000 Å-thick silver film (not shown) is formed, and a resist mask (not shown) consisting of a positive type resist is formed on the working electrode formation region and on the reference electrode formation region.

k) The working electrode 221 and the reference electrode 223 are formed using a silver etching solution (a1:1:20 aqueous solution of 29% aqueous ammonia, 31% hydrogen peroxide solution and pure water).

l) A negative type photoresist film 201c is formed on the portions other than the dent 205 and the pads 221a, 222a, 223a of the electrodes.

Figure 15C:
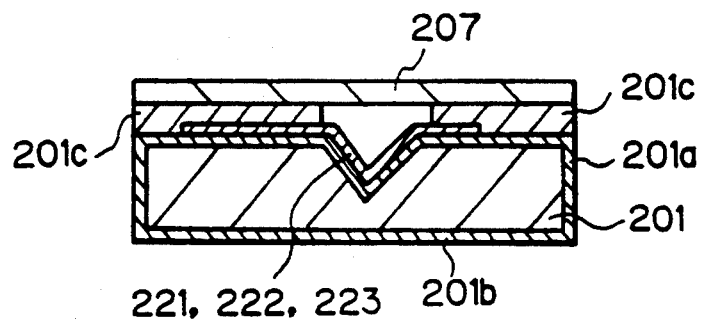

Refer to FIG. 15C.

m) The gas-permeable film 207 is formed by thermally fusing fluorinated ethylene propylene.

Figure 16A:
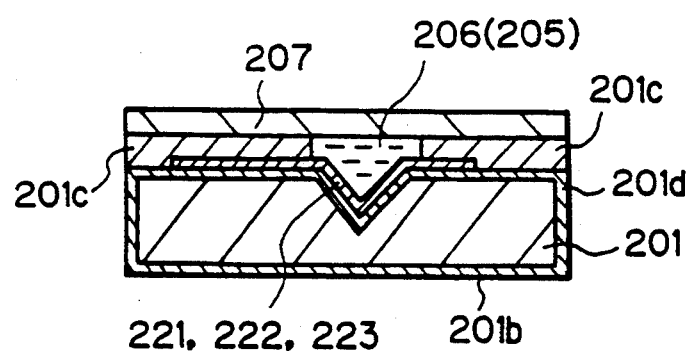
FIGS. 16A and 16B are sectional views showing step-wise the post-stage (production process of an enzyme or a microorganism immobilizing film) of the production process of the biosensor for glutamic acid according to an embodiment of the present invention.

Refer to FIG. 16A.

n) The oxygen electrode produced in the manner described above is immersed in a 0.1M aqueous potassium chloride solution, and this aqueous potassium chloride solution is subjected to pressure reduction so as to substitute the air inside the dent 205 by the potassium chloride solution. The electrolyte is filled into the dent 205.

In order to suppress electro-chemical cross-talk between the electrodes and to obtain a better performance, it is recommended to let a gel be permeated with the electrolyte, and a gel of calcium alginate is suitable for this purpose. This gel layer can be formed inside the dent 205 by introducing the calcium chloride solution into the dent 205 by deairing, allowing calcium chloride to adhere to the dent 205 by baking, again effecting deairing so as to introduce the electrolyte of O,|M KCL aqueous solution containing sodium alginate into the dents 205. Due to this process, calcium chloride is eluted and geled in sodium alginate.

Figure 16B:
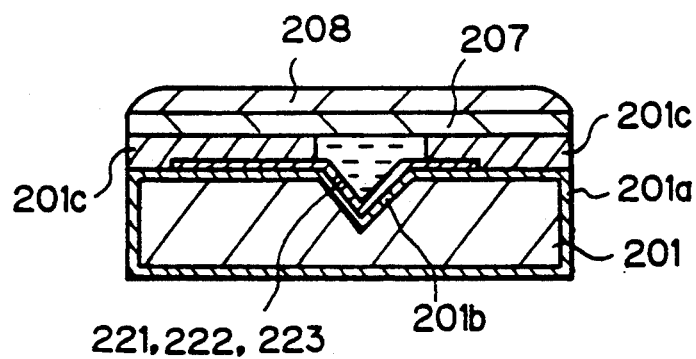
Figure 17:
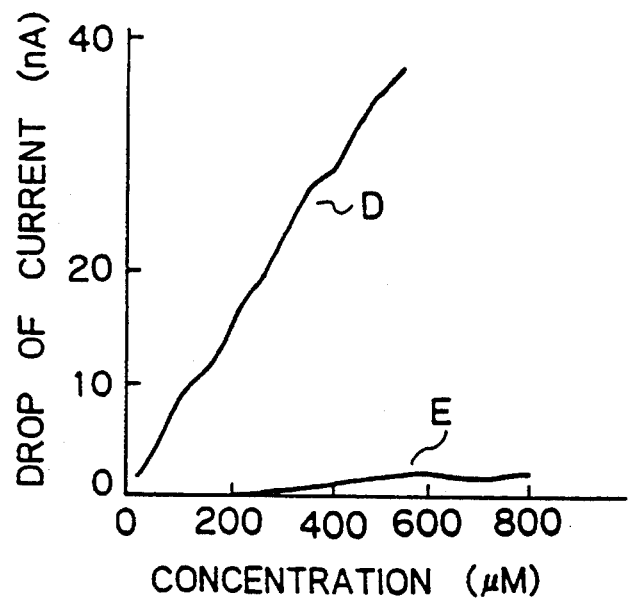
FIG. 17 shows the result of an effect confirmation test of the biosensor for glutamic acid (D) and the biosensor for lysine (E)
Figure 18:
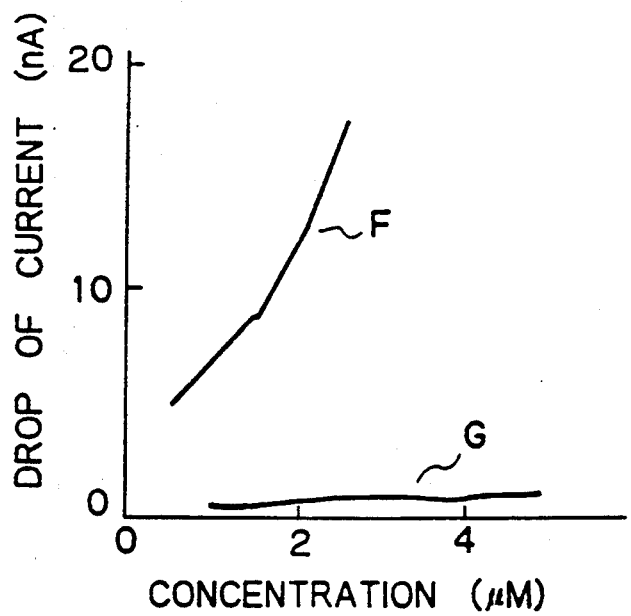
FIG. 18 shows the result of an effect confirmation test of the biosensor for histidine (F) and the biosensor for alginine (G)

Refer to FIG. 16B.

O) 1 mg of L-glutamate oxidase, a product of Yamasa Shoyu K.K., is mixed with a mixed solution containing 5% of bovine serum albumin and 5% of glutaraldehyde, and this mixed solution is coated onto the gas-permeable film 207 so as to form an enzyme- or microorganism-immobilizing film 208.

Second Embodiment (L-lysine sensor)

An oxygen sensor explained with reference to FIG. 15C is produced in exactly the same way as in the first embodiment.

p) 0.1M aqueous calcium chloride solution is introduced into the dent 205 by deairing, and is then dried naturally so as to allow calcium chloride to adhere into the dent 205.

q) Deairing is carried out once again so as to introduce an aqueous sodium alginate solution containing 0.1M potassium chloride and an independent nutrient bacteria ($1.5 \times 10^8$ ml$^{-1}$) assimilating carbon dioxide gas.

r) Air bubbles entrapped into the dents 205 simultaneously with the electrolyte are removed by centrifugal separation.

s) A mixed solution of 2 mg of L-lysine decarboxylase (a product of SIGMA Co.) with a mixed solution containing 5% of bovine serum albumin and 5% of glutaraldehyde is coated and immobilized onto the gas-permeable film 207.

The L-lysine sensor produced in this manner operates in the manner described below and detects the concentration of L-lysine. To begin with, while the sensor is immersed in a buffer solution, L-lysine is added. Then, L-lysine is decomposed by the enzyme and dissociates the carbon dioxide gas. The independent nutrient bacteria assimilating the carbon dioxide gas assimilates the carbon dioxide gas and simultaneously consumes oxygen. After all, since the amount of oxygen changes, the concentration of L-lysine can be detected.

Third Embodiment (Biosensor assembly of detecting concentrations of two kinds of amino acids)

Oxygen electrodes similar to those described above are bonded back to back. The independent nutrient bacteria is immobilized into the dent 205, and two kinds of enzymes selected from the group consisting of L-alginin decarboxylase, L-lysine decarboxylase and L-histidine decarboxylase, for example, are introduced to the gas-permeable film 207. In this manner, the concentrations of two kinds of amino acids can be detected by a single biosensor.

Fourth Embodiment (Biosensor assembly for detecting concentration of many kinds of amino acids)

A plurality of oxygen electrodes similar to those described above are integrated on a single substrate, and the independent nutrient bacteria is immobilized into the dent 205 of each of the oxygen electrodes. L-alginin decarboxylase, L-lysine decarboxylase and L-histidine decarboxylase, for example, are immobilized onto the gas-permeable film 207, or instead of immobilizing the microorganisms, L-glutamate oxidase is immobilized onto the gas-permeable film 207. In this manner, the concentration of a plurality of kinds of amino acids can be detected by a single biosensor.

Fifth and Sixth Embodiments

The fifth embodiment relates to an embodiment wherein an enzyme- or microorganism-immobilizing film having enzymes or microorganisms immobilized thereto is formed between the dent 205 of the substrate 201 and the gas-permeable film 207.

The sixth embodiment relates to another embodiment wherein an enzyme- or microorganism-immobilizing film having enzymes or microorganisms immobilized thereto is formed between the dent of the substrate and the gas-permeable film. Furthermore, an enzyme- or microorganism-immobilizing film having enzymes or microorganisms immobilized thereto is formed on the gas-permeable film 207.

These embodiments are effective when the object of measurement is a volatile matter or a gaseous matter.

As described above, the biosensor according to the present invention skillfully combines the photolithographic technique and the anisotropic etching technique widely employed in the semiconductor fabrication technology. Accordingly, the biosensor according to the present invention is extremely small in size, can be handled easily, and moreover, has excellent performance. The gas-permeable film 207 is formed by thermally fusing fluorinated ethylene propylene and is very tough. Furthermore, since the bubbles entrapped in the electrolyte solution are removed by centrifugal separation, the production yield is high.

Temperature Sensor

A preferred embodiment of the temperature sensor of the present invention is described below.

Figure 19:
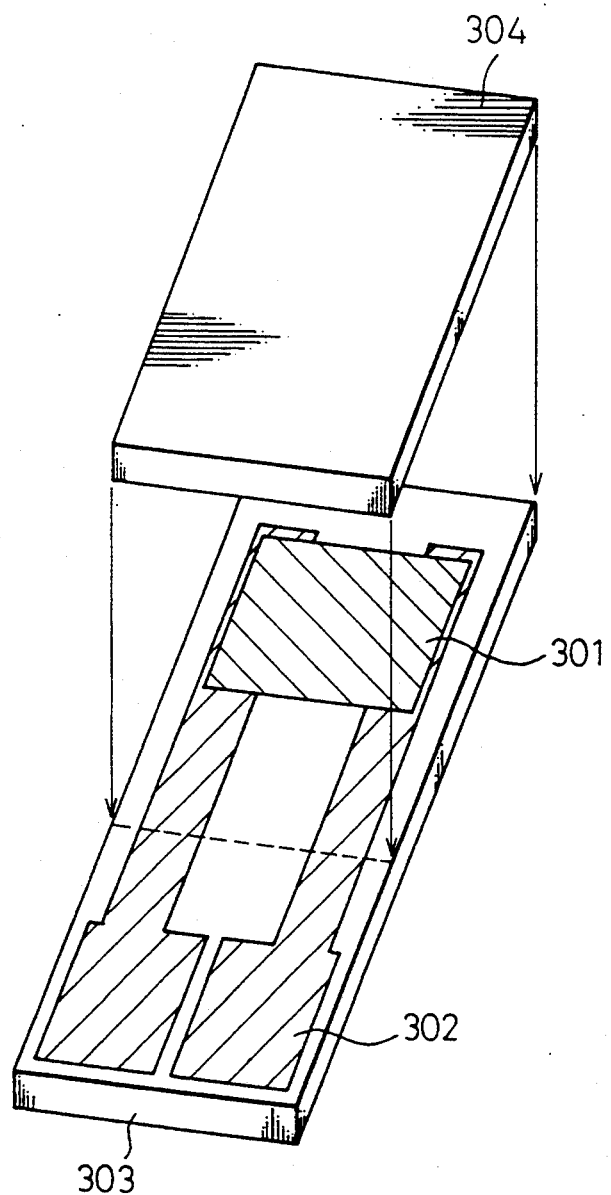
FIG. 19 is a perspective view of a basic example of a temperature sensor of the present invention.

FIG. 19 shows the structure of a basic example of the temperature sensor of the present invention. It should be noted that a plurality of temperature sensors or a combination of the temperature sensor or other type sensors may be made on an identical wafer or substrate, while only one temperature sensor is illustrated in the following figures.

A carrying planar substrate 303 has thin film conductor lines 302 and a pattern of a thin film resistor as a temperature sensing portion 301 at the ends of the thin film conductor lines 302. The thin film resistor may be made of various metals such as gold, platinum and copper. The thin film conductor lines 302 can be made of the same metal as that of the thin film resistor.

Before forming a metal resistor on a glass substrate, a suitable layer of another metal may be inserted under the metal resistor layer on the glass substrate in order to improve adhesion of the metal resistor to the glass substrate. The methods for forming a metal resistor thin film and patterning or etching the same may be selected appropriately depending on the metal of the resistor.

A thermistor exhibiting a semiconductor-like variation of resistance depending on temperature may be also used as the thin film resistor. The thermistor materials may be deposited by evaporation, sputtering, screen printing, etc.

The thin film resistor may be made by a long narrow line pattern and the conductor lines may be made by short and wide lines.

A protecting planar substrate 304 is bonded to the carrying planar substrate 303 so as to cover the temperature sensing portion 301. For example, the carrying planar substrate 303 is made of glass and the protecting planar substrate 304 is made of silicon. Either of the carrying and protecting planar substrates has a groove in which the thin film temperature sensing portion and conductor lines are seated. By selecting the depth of the groove, the temperature sensing portion 301 and the conductor lines 302 can be completely seated in the groove. The formation and patterning of the thin films (resistor and conductor lines) can be easily and precisely made by semiconductor processing technology. The productivity and reproductivity thereof are thus high.

The carrying planar substrate 303 and the protecting planar substrate 304 are directly bonded without an adhesive. For example, the both substrates are laminated and heated to a predetermined temperature, and a predetermined direct current (DC) voltage are applied between them. This is the anodic bonding. In this anodic bonding case, it is preferred that at least one of the substrates is selected to be silicon, etc., having an electrical conductivity. This direct anodic bonding provides a bonding with a sufficient strength, and is highly resistant against temperature and humidity since it does not use an adhesive.

When a plurality of temperature sensors are made in a substrate, dicing after the formation of sensor elements provides a plurality of temperature sensors having identical characteristics.

Portions of the thin film conductor lines 302 which are not covered with the protecting planar substrate 304 function as pads for electrical connection.

The substrates may be of glass, silicon or other materials.

A glass is inferior in thermal conductivity but a planar glass substrate with a large area is available at a low price. A glass substrate is superior in handling to a silicon substrate. A glass substrate allows a groove or dent to be formed by selective etching with a mixed solution comprising 50%-HF, c-$HNO_3$ and 40%-$NH_4F$ at a ratio of 1½ using a photoresist. An oxygen sensor and a pH sensor may also be made on the glass substrate.

A single silicon crystal has a thermal conductivity of 168 W/mK at 0° C., which is next to those of gold, silver, copper and aluminum, and is about three times larger than that of iron. By using such a silicon substrate as the carrying planar substrate 303 and/or the protecting planar substrate 304, a high thermal conductivity can be obtained. If a resistor is to be formed on a silicon substrate, it is preferred that an insulating layer of, for example, silicon dioxide, is inserted between the resistor and the silicon substrate. Selective etching can be easily carried out on a silicon substrate.

Diamond, alumina, aluminum nitride, etc., are other insulating materials having a high thermal conductivity. These materials can therefore be used in place of a single silicon crystal for the carrying planar substrate or the protecting planar substrate, or can be used as a material for forming an insulating coating on a single silicon crystal.

Figure 20A:
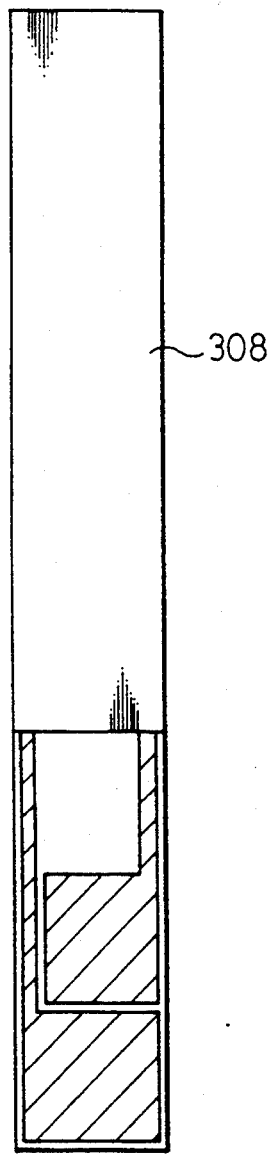
FIGS. 20A and 20B are plan views of a temperature sensor and a substrate thereof.
Figure 20B:
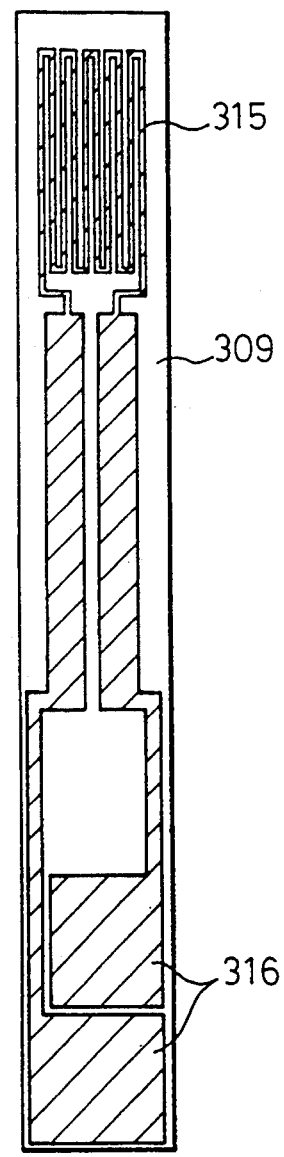

FIGS. 20A and 20B show an example of a temperature sensor of the present invention. FIG. 20A is a plan view of the sensor and FIG. 20B is a plan view of the sensor from which the protecting planar substrate 308 is removed.

In FIG. 20B, the carrying planar substrate a glass substrate 309 has a groove on the surface thereof, in which a temperature sensing portion 315 of an Au/Cr thin film resistor and thin film conductor lines 316 of Au/Cr are seated.

In FIG. 20A, the glass substrate 309 is covered with a silicon substrate 308 as the protecting planar substrate except for a lower (pad) portion of the glass substrate. The surface of the silicon substrate 308 may be coated with a $SiO_2$ layer, if necessary.

FIGS. 21A to 21F show a process for manufacturing a temperature sensor. In each of FIGS. 21A to 21F, the upper figure is a plan view and the lower figure is a cross-sectional view of a temperature sensor during some main steps of the process.

Figure 21A:
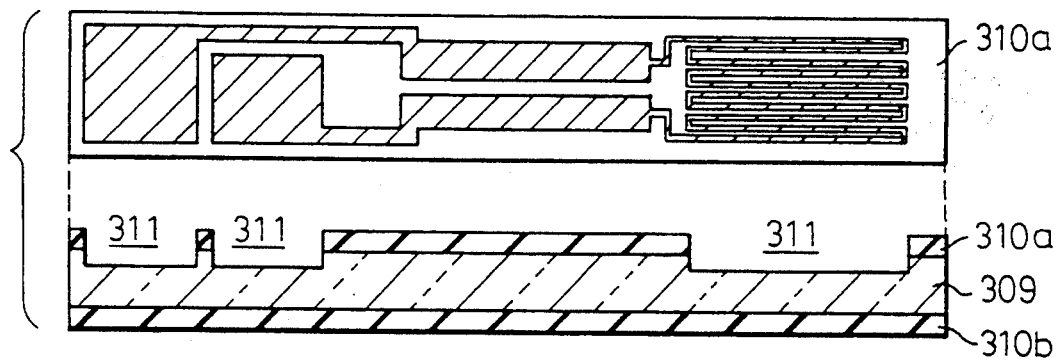
FIGS. 21A–21F show main steps of manufacturing a temperature sensor.

(A) Forming a Groove in Glass Substrate (FIG. 21A)

A polished glass substrate 309 in the form of a wafer having a thickness of 500 μm (sold by Iwaki Glass) is coated with a negative-type photoresist (for example, OMR-83 from Tokyo Ohka) by spin-coating, exposed and developed to form a resist mask 310a having an opening of a desired pattern. The opening corresponds to the pattern of the resistor 315 and conductor lines to be formed later. This negative-type photoresist is resistant to an etchant for glass such as a hydrofluoric acid solution and can be removed by boiling in sulfuric acid ($H_2SO_4$) plus hydrogen peroxide ($H_2O_2$).

The rear surface of the glass substrate 309 is also coated with a negative-type photoresist and baked at about 150° C. for about 30 minutes to form a resist mask 310b. The glass substrate 309 with the resist masks 310a and 310b is immersed in a glass etchant comprising 1 ml of 50% hydrofluoric acid (HF), 1 ml of conc. nitric acid ($HNO_3$) and 8 ml of 40% ammonium fluoride ($NH_4F$) to form a dent 311 having a depth of about 3 μm from the surface of the glass substrate 309. After the etching of the glass substrate 309, the resist masks 310a and 310b are removed from the glass substrate 309 with a mixed solution of sulfuric acid and hydrogen peroxide. The glass substrate 309 is then cleaned with a mixed solution of hydrogen peroxide and ammonia and then with pure water.

Figure 21B:
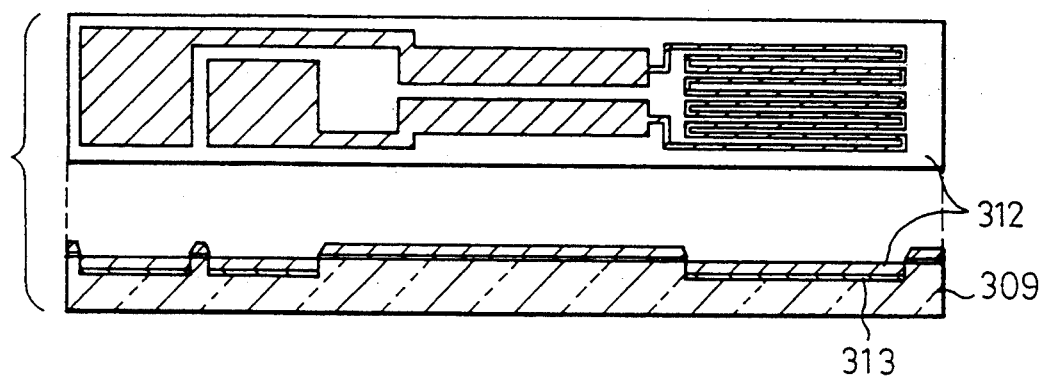

(B) Depositing Metal Layer (FIG. 21B)

On the surface of the glass substrate 309, a chromium layer 313 about 400 Å thick and then a gold layer 312 about 4000 Å thick are evaporated. The chromium layer 313 is provided to improve the adhesion of the gold layer 312 to the glass substrate 309.

Figure 21C:
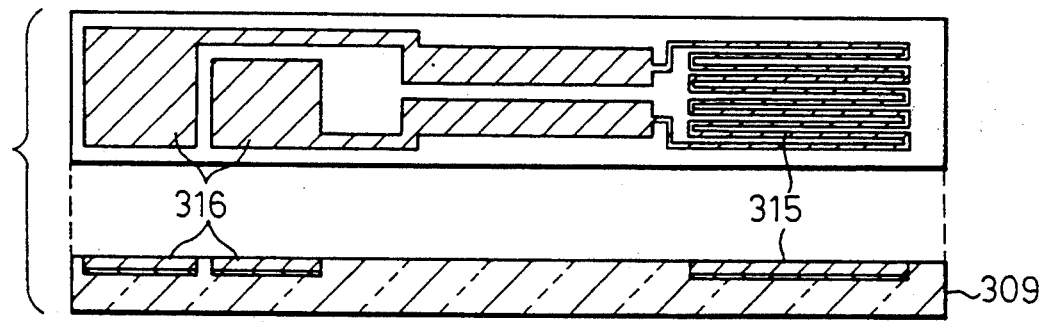

(C) Patterning Conductor (FIG. 21C)

A positive-type photoresist (for example, OFPR-800 sold by Tokyo Ohka) is spin-coated on the deposited metal layers of the glass substrate and is then patterned with the same mask as used in the step (B) to obtain a resist mask which is an inverse to the pattern in FIG. 21A.

The glass substrate 309 is then immersed in a gold etchant comprising 4g of potassium iodide, 1 g of iodine and 40 ml of water to etch the gold layer 312 outside of the groove 311. After the gold layer 312 is etched, the glass substrate is immersed in acetone to remove the resist mask of the positive-type photoresist. The glass substrate 309 is then immersed in a chromium etchant comprising 1 g of sodium hydroxide (NaOH) and 2 g of potassium ferricyanide $K_3Fe(CN)_6$ in 8 ml water to etch the chromium layer 313. Where the gold layer 312 covers the chromium layer 313, the gold layer 312 and chromium layer 313 are not etched to leave patterns of the gold and chromium layers.

Thus, the glass substrate on which a temperature sensor is mounted is finished.

The following steps form a protecting planar substrate.

Figure 21D:
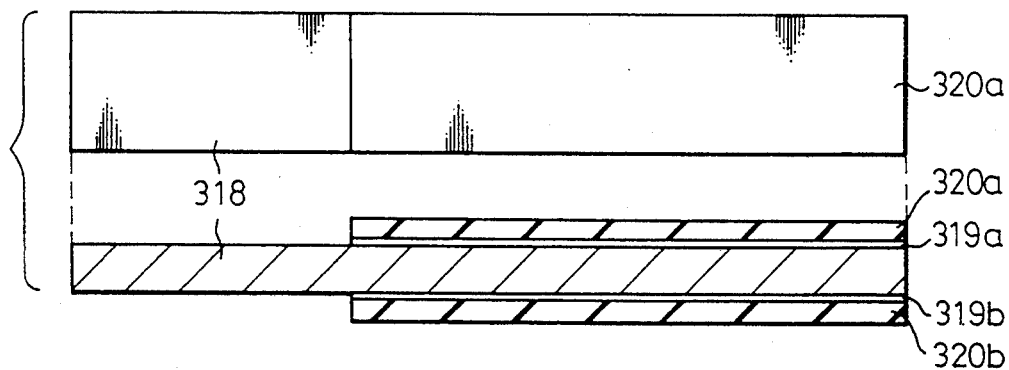

(D) Forming Mask (FIG. 21D)

A (100) plane of a clean silicon substrate 318 having a thickness of about 350 μm is thermally oxidized to form a $SiO_2$ layer 319 over all the surfaces of the silicon substrate 318. The $SiO_2$ layer 319 is used as a mask for etching the silicon substrate 318.

Both surfaces of the silicon substrate 318 are coated with a negative-type photoresist (for example, OMR-83 sold by Tokyo Ohka), which is exposed, developed and rinsed to obtain etching resist masks 320a and 320b as shown in FIG. 21D.

If both resist masks have corresponding openings, the resist masks may be used to form a through hole. If a resist mask on one side has an opening but the opposite resist mask does not have a corresponding opening, the resist masks may be used to form a dent having a depth half of the total thickness of the substrate. In manufacturing a temperature sensor, only a through hole is formed on the substrate 318. Nevertheless, a dent is also formed if a pH sensor and/or an oxygen sensor are manufactured on the same substrate 318.

The silicon substrate 318 with the resist masks 320g and 320b is immersed in a $SiO_2$ enchant comprising 1 ml of 50%-HF and 6 ml of 40%-$NH_4F$ to selectively remove the $SiO_2$ layers 319a and 319b where they are not covered with the resist masks 320a and 320b. After the $SiO_2$ layer 319 is etched, the resist masks 320a and 320b are removed by a mixed aqueous solution of conc. sulfuric acid and hydrogen peroxide.

Figure 21E:
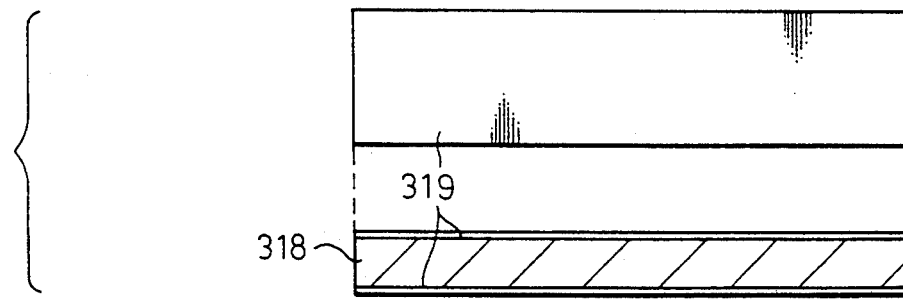

(E) Forming Opening (FIG. 21E)

The silicon substrate 318 is immersed in an aqueous 35%-KOH solution at 80° C. to perform an anisotropic etching. By this anisotropic etching, the silicon substrate 318 is etched where it is not covered with the $SiO_2$ layer 319. The etching is continued until a through hole is formed where the opening of the $SiO_2$ layer is formed on both sides of the Si substrate 318. In this etching, if the substrate has an opening of the $SiO_2$ layer only on one side, a dent is formed to have a depth about half of the thickness of the Si substrate 318.

FIGS. 21D and 21E illustrate only one sensor element. If a plurality of temperature sensors are formed on a wafer, the plurality of the protecting planar substrates are simultaneously shaped. If an oxygen sensor and/or a pH sensor are also made on the Si substrate, dents in addition to the through hole are formed.

(F) Bonding (FIG. 21F, FIGS. 22A to 22C)

Figure 22A:
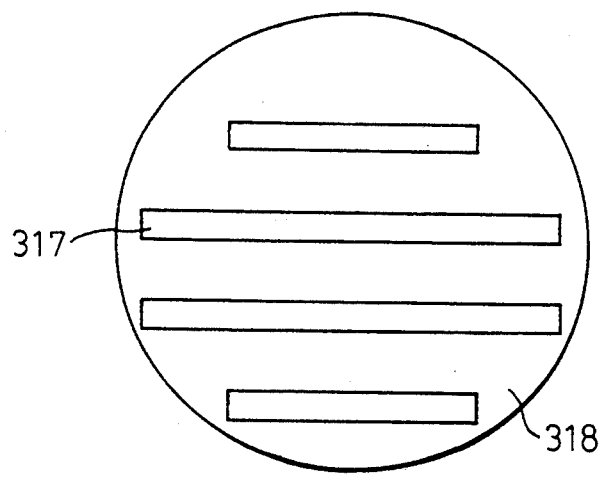
FIGS. 22A–22C show carrying and protecting substrates in the form of a wafer and alignment thereof.

FIG. 22A is a plan view of a wafer corresponding to FIG. 21E. By the etching of silicon substrate in FIG. 21E, a through hole or window 317 in the form of strip is made in the wafer.

Figure 22B:
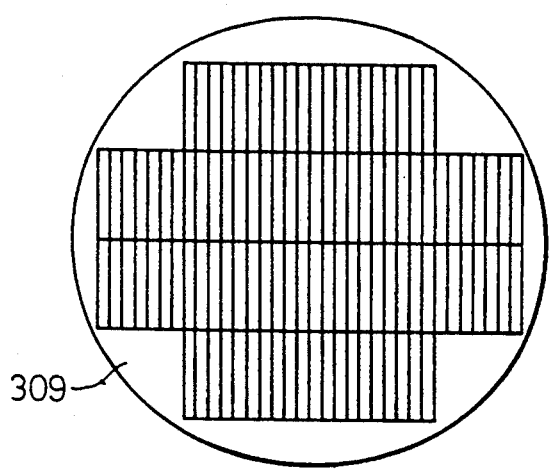

FIG. 22B is a plan view of a wafer of a glass substrate 309 corresponding to FIG. 21C. The windows 317 of the wafer 318 shown in FIG. 22A correspond to the portions of the bonding pads of the carrying planar substrates 309 in FIGS. 21C and 22B.

Figure 22C:
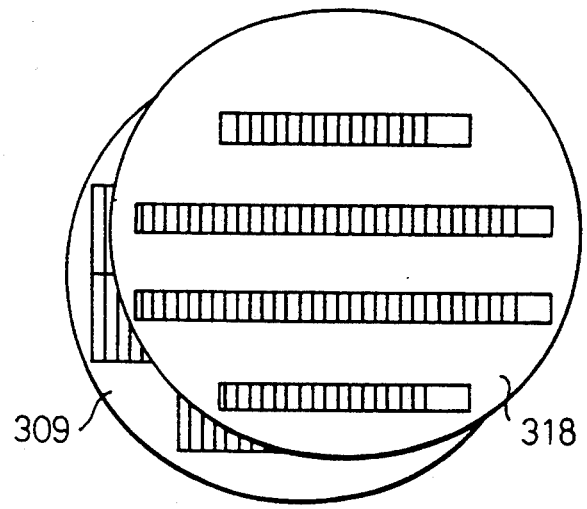

The glass substrate 309 on which a temperature sensor is mounted and the silicon substrate 318 in which the windows 317 are formed are cleaned with supersonic waves and then laminated and aligned with each other (FIG. 22C). The laminated substrates are sandwiched with a pair of conducting plates.

Figure 21F:
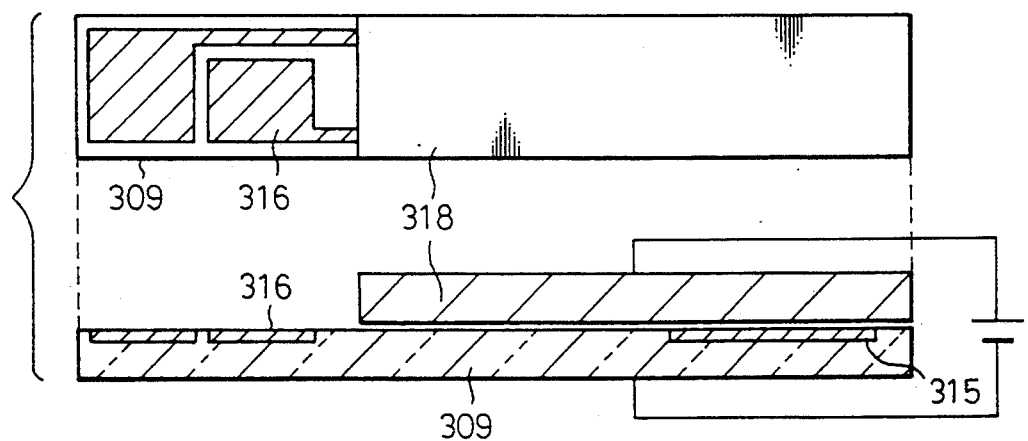

As seen in FIG. 21F, after the alignment, a DC voltage of about 1200 V is applied between the silicon substrate 318 and the glass substrate 309 at about 250° C., so that the substrates are anodic bonded with each other. Here, a negative potential is applied to the glass substrate 309.

By this anodic bonding, the glass substrate 309 and the silicon substrate 318 are bonded as if they were wet, so that a air tight bonding is obtained. Nevertheless, a portion of the glass substrate 309 where the groove is formed is open. If it is desirable to make the portion air tight, the open portion may be sealed with a resin, for example.

The bonded substrates are diced into a plurality of chips, i.e., the temperature sensors, for example, 2 mm×15 mm size.

Thus, temperature sensors are obtained.

Figure 23:
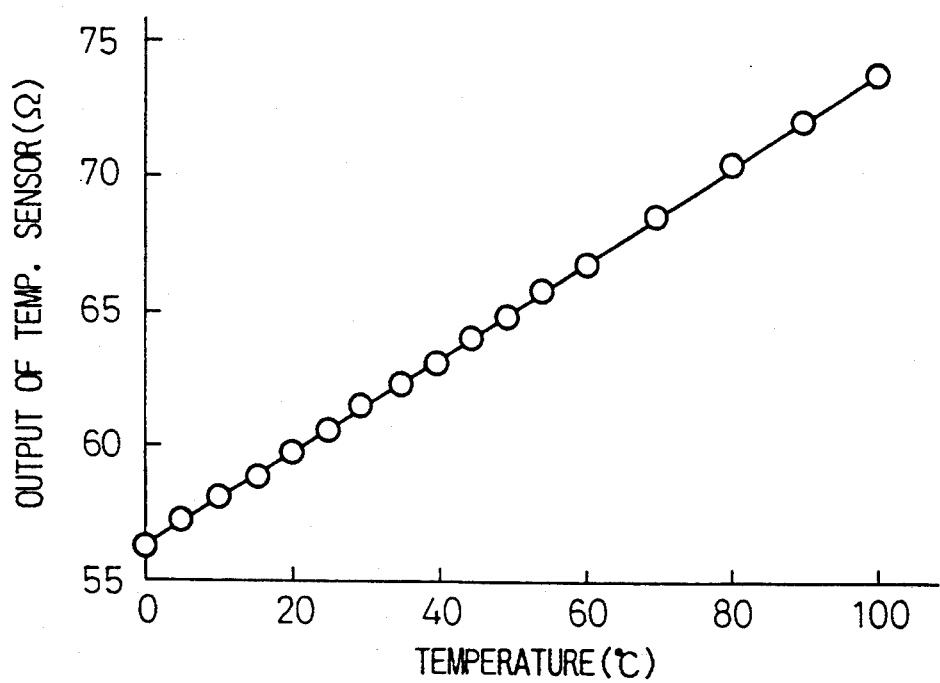
FIG. 23 shows the characteristic of a temperature sensor.

FIG. 23 shows the characteristics of the thus obtained temperature sensor. In FIG. 23, the abscissa represents the temperature in ° C. and the ordinate represents the resistance of the thin film resistor in $\Omega$. FIG. 23 demonstrates that a linear characteristic of the temperature sensor is obtained from 0° C. to 100° C.

FIGS. 24A to 24D show other examples of the substrates and the groove of the temperature sensor of the present invention.

Figure 24A:
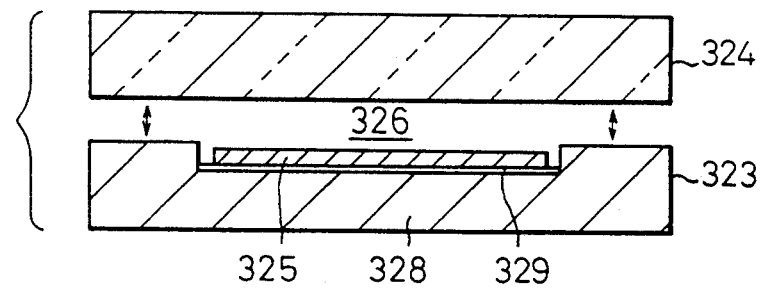
FIGS. 24A–24D show other embodiments of temperature sensors.

In FIG. 24A, the temperature sensor-mounted substrate 323 is a silicon wafer 328 in which only a portion of conductor layers 325 (i.e., within the groove 326) is covered with a $SiO_2$ layer 329. The protecting substrate 324 is a glass substrate 327.

Figure 24B:
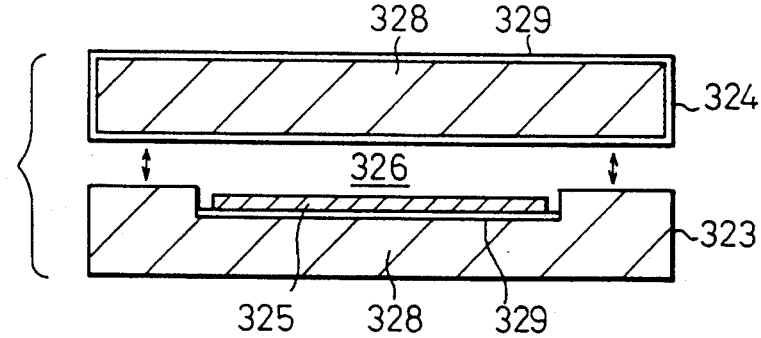

In FIG. 24B, the temperature sensor-mounted substrate 323 is the same as in FIG. 24A. The protecting substrate 324 is also a silicon wafer 328 completely covered with a $SiO_2$ layer 329. The direct bonding is effected between the covering $SiO_2$ layer 329 and the carrying silicon wafer 328.

Figure 24C:
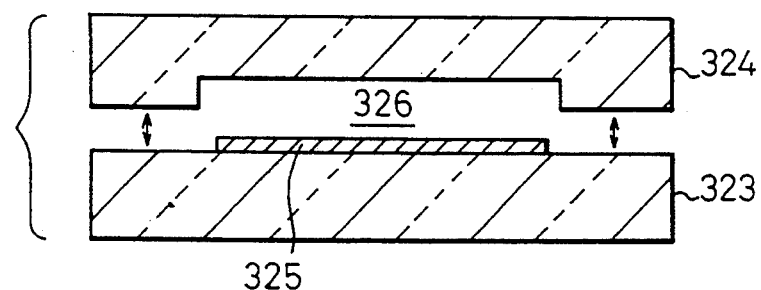

In FIG. 24C, both substrate are glass substrates, and the groove 326 for conductor patterns are formed on the protecting substrate 324.

Figure 24D:
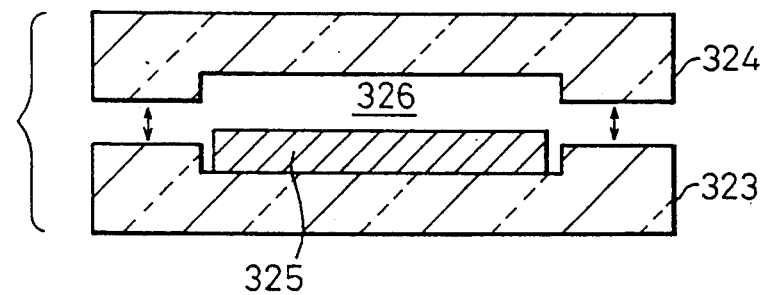

In FIG. 24D, both substrates are glass substrates and the groove 326 for conductor patterns is formed in both glass substrates 323 and 324.

Oxygen Sensor with Temperature Sensor

As described before, a temperature sensor of the present invention can be advantageously combined with another sensor such as an oxygen sensor.

Figure 25A:
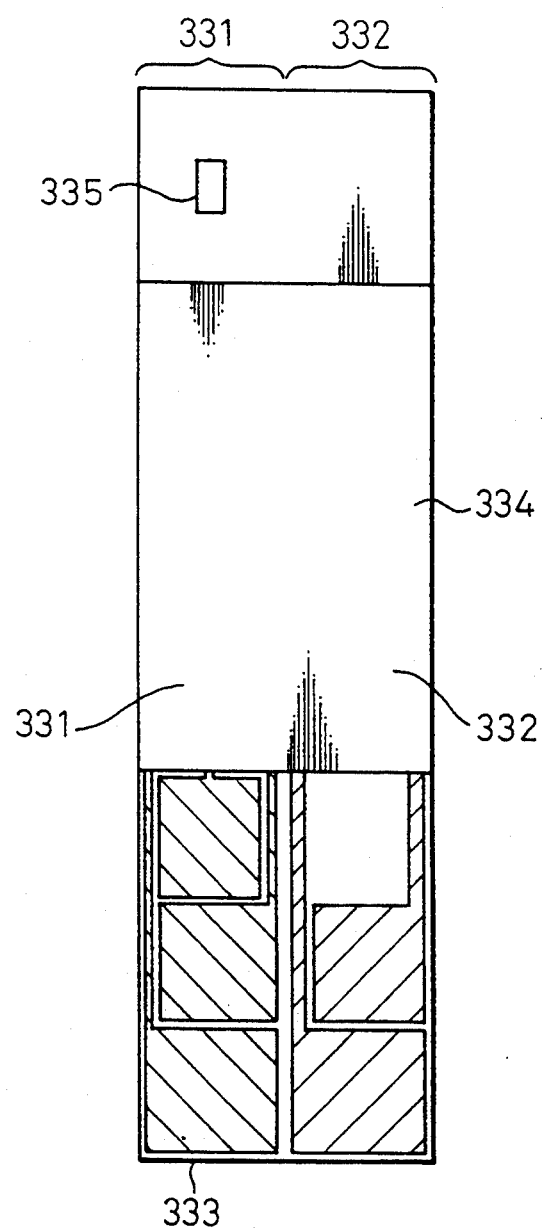
FIGS. 25A–25C show a complex sensor comprising an oxygen sensor and a temperature sensor.
Figure 25B:
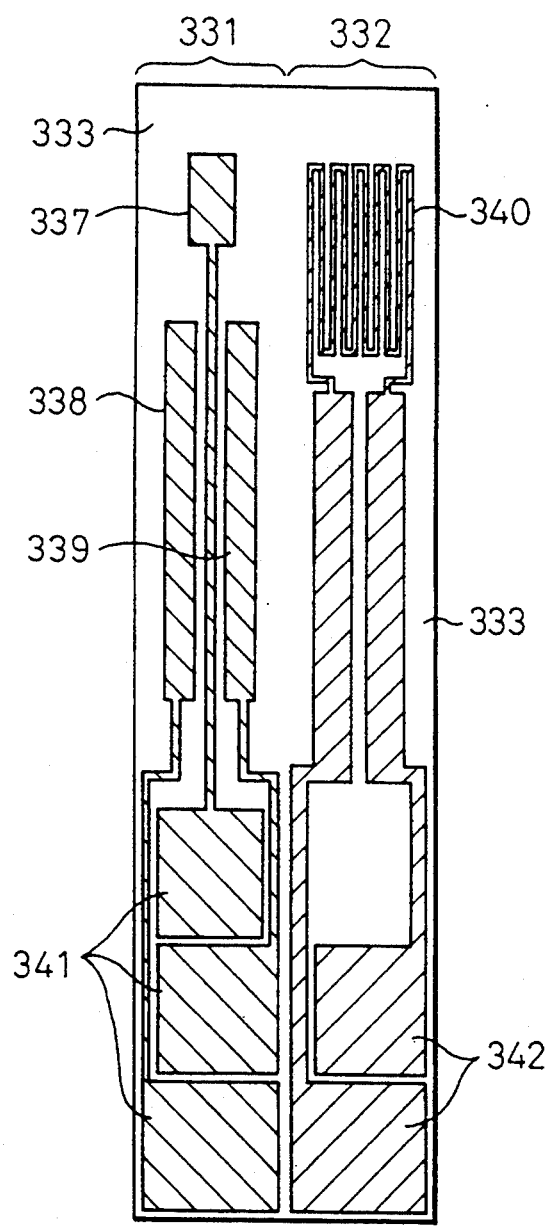
Figure 25C:
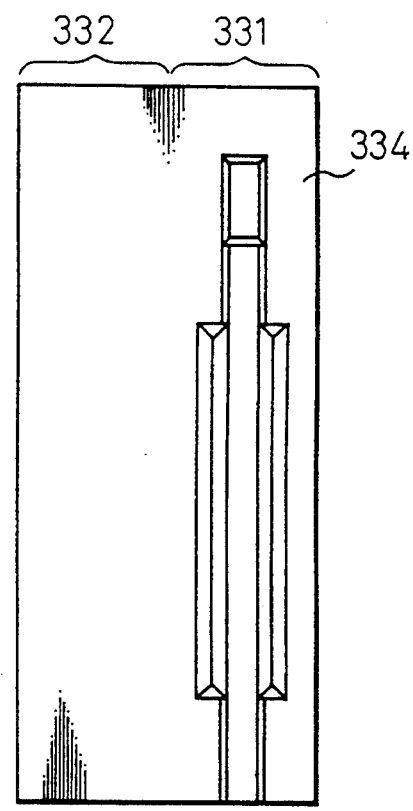

FIGS. 25A to 25C show such a combined or integrated sensor. FIG. 25A is a plan view of the combined sensor, FIGS. 25B and 25C are plan views of two substrates before they are bonded. The surfaces of the two substrates shown in FIG. 25B and 25C are those to be bonded to each other.

In FIG. 25A, a pair of an oxygen sensor 331 and a temperature sensor 332 are formed on a planar insulating substrate of a glass substrate 333. To this planar glass substrate with the two sensors formed thereon, a silicon substrate 334 having a planar surface is directly bonded by anodic bonding. A gas permeable film 335 is provided on the silicon substrate 334 above the working electrode of the oxygen sensor 331.

FIG. 25B shows the glass substrate 333 on which two sensors are formed but the silicon substrate 334 is not yet bonded. The temperature sensor 332 comprises a temperature sensing portion 340 and conductor lines with pads 342, both made of a metal layer. The oxygen sensor 331 comprises a working electrode 337, a counter electrode 338, a reference electrode 339, and conductor lines with pads 341. FIG. 25C shows the silicon substrate 334 on the side to be bonded to the glass substrate. FIG. 25C corresponds to FIG. 4. The details of both temperature and oxygen sensors were described herein before.

It is clear that the oxygen sensor of the above combined sensor can be modified to be a biosensor, as described before.

Oxygen Sensor and pH Sensor with Temperature Sensor

Figure 26A:
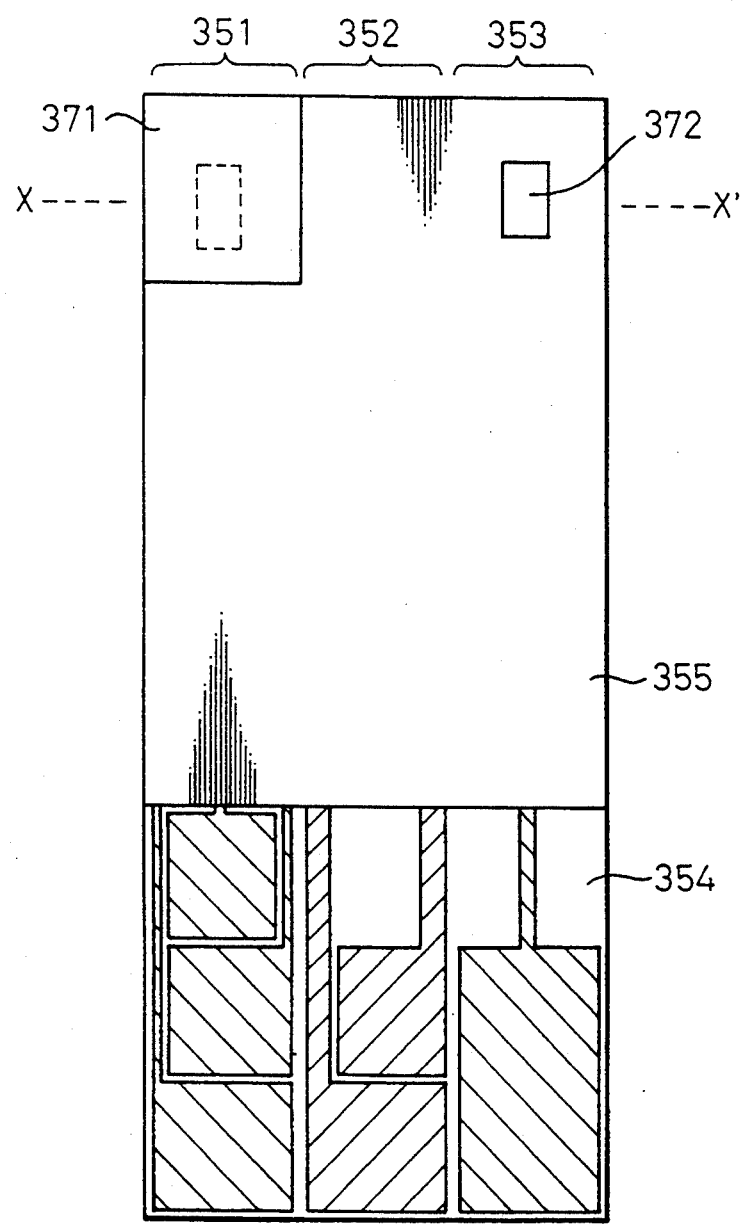
FIGS. 26A–26C show a complex sensor comprising an oxygen sensor, a pH sensor and a temperature sensor.
Figure 26B:
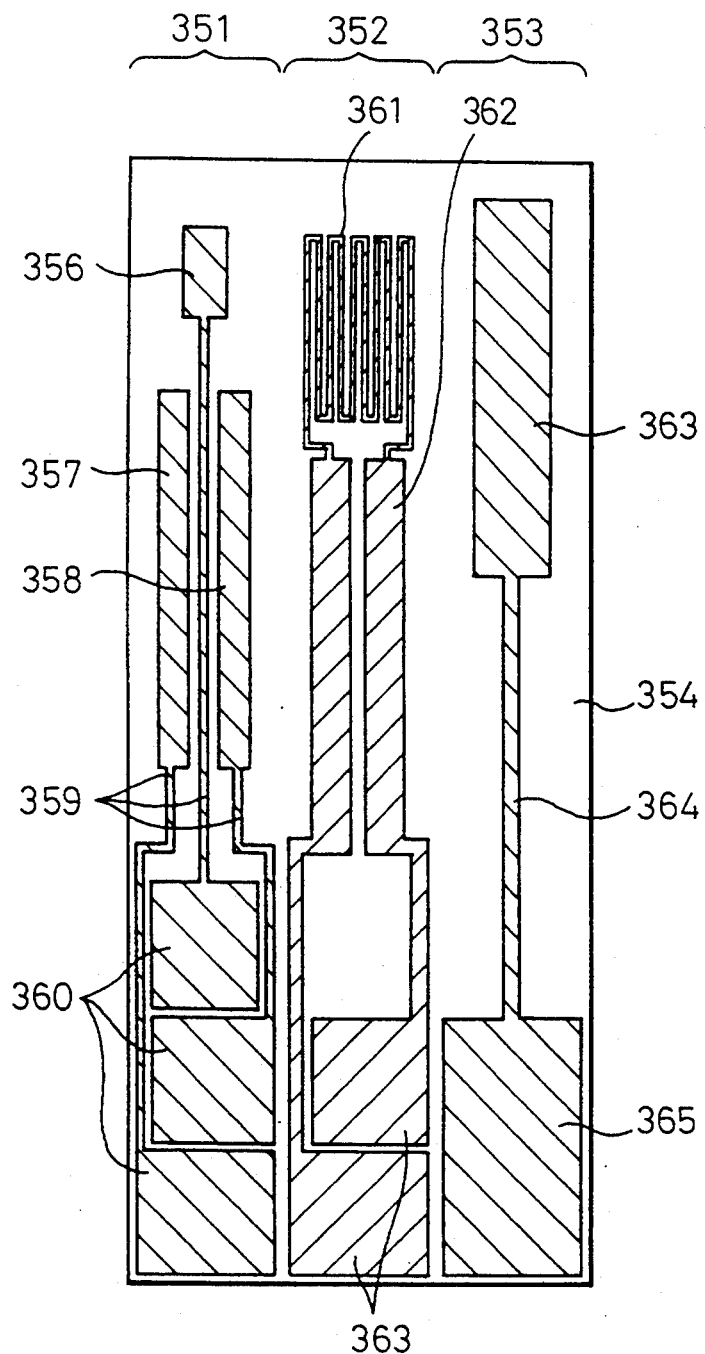
Figure 26C:
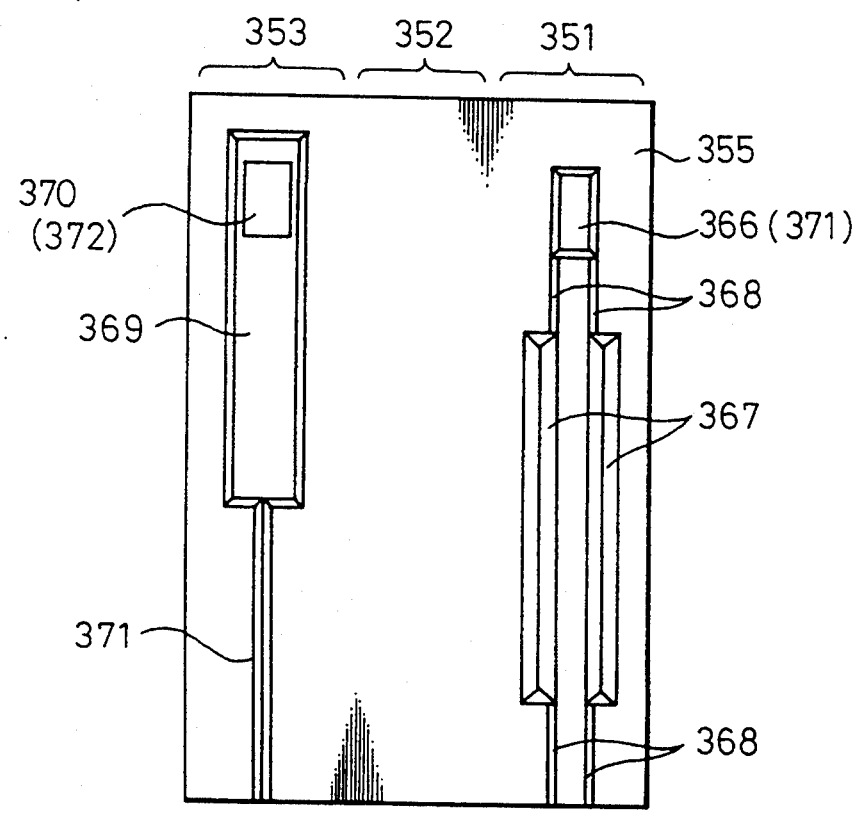

FIGS. 26A to 26C show another combined sensor comprising an oxygen, sensor, a pH sensor and a temperature sensor.

FIG. 26A is a plan view of the combined sensor, FIGS. 26B and 26C are plan view of two substrates before they are bonded. The surfaces of the two substrates shown in FIGS. 26B and 26C are those to be bonded to each other.

In FIG. 26A, a set of an oxygen sensor 351, a temperature sensor 352 and a pH sensor 353 are formed on a planar glass substrate 354. To this planar glass substrate with a set of three sensors formed thereon, a silicon substrate 355 having a planar surface is directly bonded by anode bonding. The portion where the oxygen sensor 351 and temperature sensor 352 are formed is similar to FIGS. 25A to 25C.

Referring to FIG. 26B, the $O_2$ sensor 351 comprises a working electrode 356, a counter electrode 357, a reference electrode 358, leads 359 and pads 360, all of which are a gold layer except for the reference electrode 358. The reference electrode 358 is made of silver/silver chloride but a gold layer is inserted under the silver/silver chloride of the reference electrode on the glass substrate 354. The temperature sensor comprises a thin film resistor 361, leads 362 and pads 363, all of which are a gold layer. The pH sensor comprises a reference electrode 363, a lead 364 and a pad 365. The reference electrode 363 is made of silver/silver chloride but a gold layer is inserted under the silver/silver chloride of the reference electrode on the glass substrate 354. The lead 364 and the pad 365 are a gold layer.

Referring to FIG. 26C, the silicon substrate 355 has dents 366 and 367 for storing an electrolyte and grooves 368 for injecting an electrolyte into the dents 366 and 367, in the portion 351 of the $O_2$ sensor, and has a dent 369 for storing an electrolyte and a groove 371 for injecting an electrolyte into the dent 369, in the portion 353 of the pH sensor. The dent 366 penetrates through the silicon substrate 355, and a gas permeable resin film 371 is provided on the opposite exterior side of the substrate 355 to cover the bottom of the dent 366 which confronts the working electrode 356. There is also a through-hole 370 at a portion of the dent 369, and a hydrogen ion selective glass film 372 is provided on the opposite exterior side of the substrate 355 to cover the through hole 370.

Figure 27A:
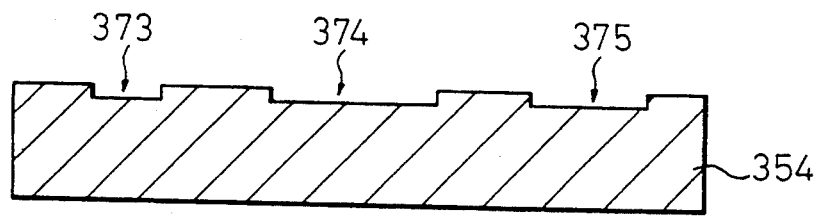
FIGS. 27A–27C show cross sections of the two substrates of the complex sensor and a cross section of the complex sensor, all cut along the line X–X' in FIG. 26A.
Figure 27B:
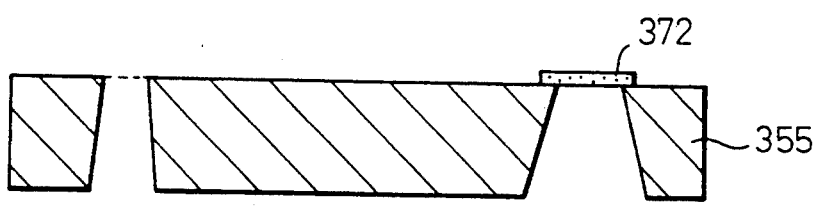
Figure 27C:
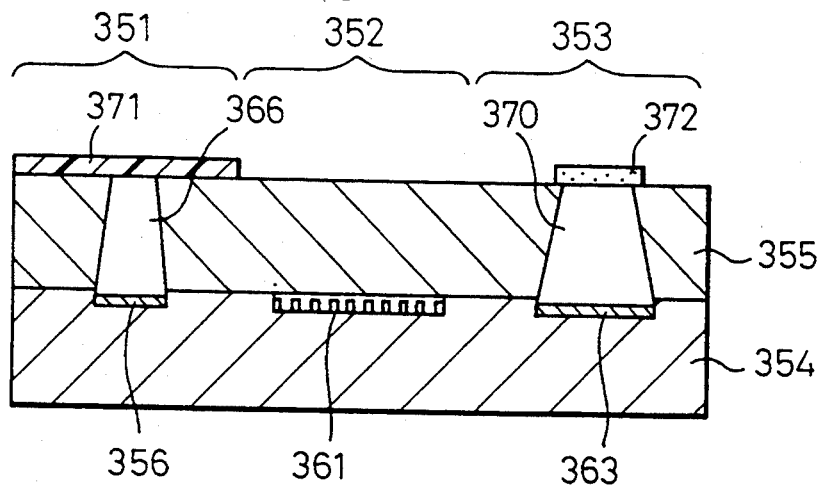

FIGS. 27A to 27C show cross sections of the two substrates of the combined sensor and a cross section of the combined sensor, cut along the line X-X' in FIG. 26A.

Referring to FIG. 27A, the glass substrate 354 is subject to a selective etching to form grooves 373 to 375 for seating the gold layers and the reference electrodes. The selective etching can be conducted by first forming a photoresist pattern using a known photolithography and then a hydrofluoric acid solution etching. After the photoresist is removed, chromium (400 Å thick) and then gold (4000 Å thick) are deposited and patterned in the same manner as described before. Then, the reference electrodes 363 and 358 are made of silver/silver chloride in the manner described before.

Referring to FIG. 27B, a silicon substrate 355 is first subject to thermal oxidation to form a surface oxide ($SiO_2$) layer. The $SiO_2$ layer is partially etched off to make an opening which has a pattern of one of the dents, grooves and hole. This silicon substrate is immersed in an etching solution to conduct anisotropic etching, to thereby form said one of the dents, grooves and hole. The above process from the thermal oxidation to the anisotropic etching is repeated to form all of the dents, grooves and hole. After all dents, grooves and holes are formed, the surface oxide layer is etched off except for a portion covering the through-hole 370. The remaining portion of the silicon oxide layer (1 μm thick) is the hydrogen ion selective glass film 372. The surface oxide layer is removed to facilitate anodic bonding of the silicon substrate to the glass substrate.

Referring to FIG. 27C, the thus formed glass substrate 354 and silicon substrate 355 are then directly bonded by applying a DC electric voltage between the substrates. A gas permeable resin film 371 (for example, fluorinated ethylene propylene film having a thickness of 12 μm) is adhered to the exterior surface of the silicon substrate 355 to cover the opening of the dent 366.

Thus, the combined sensor comprising a pH sensor 353, an $O_2$ sensor 351 and a temperature sensor 352 as shown in FIGS. 26A and 27C is obtained. Appropriate electrolytes are injected into the dents in the $O_2$ sensor and the hole in the pH sensor, preferably just before use. An example of the electrolyte for the pH sensor is a 0.1M aqueous potassium chloride solution. An example of the electrolyte for the $O_2$ sensor is a 0.1M aqueous potassium chloride solution.

We claim:

1. A complex sensor including an oxygen sensor and a temperature sensor, comprising:
   first and second substrates directly bonded to each other, the bonded first and second substrates having a first section for an oxygen sensor and a second section for a temperature sensor, the first and second sections being separated from each other,
   a) the first section further comprising:
      at least two electrodes including a working electrode and a counter electrode, formed on the first substrate,
      at least one dent formed on the second substrate and confronting the two electrodes, for storing an electrolyte, the dent confronting the electrode constituting the working electrode having a through-hole extending to the side opposite to the first substrate, and
      a gas permeable film formed on the second substrate and covering the through-hole, and
   b) the second section further comprising:
      a thin film resistor formed between the first and second substrates.

2. A complex sensor according to claim 1, wherein an enzyme- or microorganism-immobilized film is provided on the gas permeable film, so that the oxygen sensor acts as a biosensor.

3. A complex sensor including an oxygen sensor, a temperature sensor and a pH sensor, comprising:
   first and second substrates directly bonded to each other, the bonded first and second substrates having a first section for an oxygen sensor, a second section for a temperature sensor and a third section for a pH sensor, the first, second and third sections being separated from each other,
   a) the first section further comprising:
      at least two electrodes including a working electrode and a counter electrode, formed on the first substrate,
      at least one dent formed on the second substrate and confronting the two electrodes, for storing an electrolyte, the dent confronting the electrode constituting the working electrode having a through-hole extending to the side opposite to the first substrate, and
      a gas permeable film formed on the second substrate and covering the through-hole,
   b) the second section further comprising:
      a thin film resistor formed between the first and second substrates, and
   c) the third section further comprising:
      a reference electrode formed on the first substrate,
      a dent formed on the second substrate and confronting the reference electrode for storing an electrolyte, the dent piercing the second substrate at at least a part of the dent, and
      a glass film formed on the second substrate and covering the pierced part of the hole, the glass film being hydrogen ion selective.

4. A complex sensor according to claim 3, wherein an enzyme- or microorganism-immobilized film is provided on the gas permeable film so that the oxygen sensor acts as a biosensor.

5. A complex sensor comprising first and second substrates bonded to each other, the bonded first and second substrates having a first section for an oxygen sensor and a second section for a temperature sensor.

6. A complex sensor according to claim 5, wherein said first and second substrates further include a third section for a pH sensor.

* * * * *

UNITED STATES PATENT AND TRADEMARK OFFICE
CERTIFICATE OF CORRECTION

PATENT NO. : 5,431,806
DATED : JULY 11, 1995
INVENTOR(S) : Hiroaki SUZUKI, et al.

It is certified that error appears in the above-indentified patent and that said Letters Patent is hereby corrected as shown below:

Col. 10, line 23, "11/20" should be --1/1/20--.

Col. 11, line 17, "(11)" should be --(II)--;
line 23, "(11)" should be --(II)--;
line 37, "(11)" should be --(II)--.

Col. 13, TABLE 1, fourth column, line 59, insert -- ◎ --;

TABLE 1, second, third and fourth columns, line 61, insert -- ◎ --; -- ◎ --; -- ◎ --;

line 63, ": very strong" should be -- ◎ : very strong--.

Col. 22, line 46, "1 1/8" should be --1/1/8--.

Signed and Sealed this

Third Day of October, 1995

Attest:

BRUCE LEHMAN

*Attesting Officer*    *Commissioner of Patents and Trademarks*